(12) United States Patent
Killion et al.

(10) Patent No.: US 8,506,592 B2
(45) Date of Patent: Aug. 13, 2013

(54) METHOD AND SYSTEM FOR SEALING PERCUTANEOUS PUNCTURES

(75) Inventors: Douglas P. Killion, Maple Grove, MN (US); Robert M. Vidlund, Forest Lake, MN (US); Christopher U. Cates, Atlanta, GA (US)

(73) Assignee: St. Jude Medical, Inc., St. Paul, MN (US)

( * ) Notice: Subject to any disclaimer, the term of this patent is extended or adjusted under 35 U.S.C. 154(b) by 655 days.

(21) Appl. No.: 12/461,775

(22) Filed: Aug. 24, 2009

(65) Prior Publication Data

US 2010/0211000 A1  Aug. 19, 2010

Related U.S. Application Data

(60) Provisional application No. 61/190,085, filed on Aug. 26, 2008, provisional application No. 61/213,407, filed on Jun. 4, 2009.

(30) Foreign Application Priority Data

Aug. 20, 2009  (WO) ................ PCT/US2009/054492

(51) Int. Cl.
*A61B 17/08*  (2006.01)
(52) U.S. Cl.
USPC ........................................ 606/213
(58) Field of Classification Search
USPC .......................... 606/213–216, 139
See application file for complete search history.

(56) References Cited

U.S. PATENT DOCUMENTS

| | | | |
|---|---|---|---|
| 4,744,364 A | 5/1988 | Kensey | |
| 4,779,611 A | 10/1988 | Grooters et al. | |
| 4,852,568 A | 8/1989 | Kensey | |
| 4,890,612 A | 1/1990 | Kensey | |
| 4,929,246 A | 5/1990 | Sinofsky | |
| 5,021,059 A | 6/1991 | Kensey et al. | |
| 5,061,274 A | 10/1991 | Kensey | |
| 5,104,375 A | 4/1992 | Wolf et al. | |
| 5,108,421 A | 4/1992 | Fowler | |
| 5,127,393 A * | 7/1992 | McFarlin et al. | ............. 600/114 |
| 5,129,882 A | 7/1992 | Weldon et al. | |
| 5,192,300 A | 3/1993 | Fowler | |
| 5,192,302 A | 3/1993 | Kensey et al. | |

(Continued)

FOREIGN PATENT DOCUMENTS

WO  0002488  1/2000
WO  WO 02/072188 A1  9/2002

OTHER PUBLICATIONS

International Search Report and Written Opinion issued in International Application No. PCT/US2009/054492 mailed Apr. 6, 2010 (23 pages).

*Primary Examiner* — Gregory Anderson
(74) *Attorney, Agent, or Firm* — Holland & Hart

(57) ABSTRACT

A device for sealing a puncture in a patient includes a sealing component including an elongate control member configured to pass through a puncture in skin of a patient. The sealing component also includes an expandable member disposed near a distal end of the control member, and a tip releasably attached to the elongate control member distal to the expandable member. The device also includes a sealing material delivery component including a delivery tube through which the control member of the sealing component is configured to extend. The delivery tube is configured to deliver sealing material through an opening in a distal end of the delivery tube.

35 Claims, 21 Drawing Sheets

(56) References Cited

U.S. PATENT DOCUMENTS

| | | |
|---|---|---|
| 5,221,259 A | 6/1993 | Weldon et al. |
| 5,222,974 A | 6/1993 | Kensey et al. |
| 5,275,616 A | 1/1994 | Fowler |
| 5,282,827 A | 2/1994 | Kensey et al. |
| 5,324,306 A | 6/1994 | Makower et al. |
| 5,330,446 A | 7/1994 | Weldon et al. |
| 5,342,393 A | 8/1994 | Stack |
| 5,350,399 A | 9/1994 | Erlebacher et al. |
| 5,354,271 A | 10/1994 | Voda |
| 5,370,660 A | 12/1994 | Weinstein et al. |
| 5,383,896 A | 1/1995 | Gershony et al. |
| 5,383,899 A | 1/1995 | Hammerslag |
| RE34,866 E | 2/1995 | Kensey et al. |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen |
| 5,441,517 A | 8/1995 | Kensey et al. |
| 5,443,481 A | 8/1995 | Lee |
| 5,454,833 A | 10/1995 | Boussignac et al. |
| 5,462,561 A | 10/1995 | Voda |
| 5,464,396 A | 11/1995 | Barta et al. |
| 5,478,352 A | 12/1995 | Fowler |
| 5,486,195 A | 1/1996 | Myers et al. |
| 5,496,332 A | 3/1996 | Sierra et al. |
| 5,507,744 A | 4/1996 | Tay et al. |
| 5,531,759 A | 7/1996 | Kensey et al. |
| 5,540,715 A | 7/1996 | Katsaros et al. |
| 5,571,181 A | 11/1996 | Li |
| 5,591,204 A | 1/1997 | Janzen et al. |
| 5,591,205 A | 1/1997 | Fowler |
| 5,593,422 A | 1/1997 | Muijs Van De Moer et al. |
| 5,601,602 A | 2/1997 | Fowler |
| 5,620,461 A | 4/1997 | Muijs Van De Moer et al. |
| 5,626,601 A | 5/1997 | Gershony et al. |
| 5,630,833 A | 5/1997 | Katsaros et al. |
| 5,645,566 A | 7/1997 | Brenneman et al. |
| 5,649,959 A | 7/1997 | Hannam et al. |
| 5,653,730 A | 8/1997 | Hammerslag |
| 5,665,106 A | 9/1997 | Hammerslag |
| 5,665,107 A | 9/1997 | Hammerslag |
| 5,674,231 A | 10/1997 | Green et al. |
| 5,676,689 A | 10/1997 | Kensey et al. |
| 5,681,334 A | 10/1997 | Evans et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,132 A | 3/1998 | Van Tassel et al. |
| 5,728,134 A | 3/1998 | Barak |
| 5,741,223 A | 4/1998 | Janzen |
| 5,746,755 A | 5/1998 | Wood et al. |
| 5,766,206 A | 6/1998 | Wijkamp et al. |
| 5,782,860 A | 7/1998 | Epstein et al. |
| 5,810,810 A | 9/1998 | Tay et al. |
| 5,810,846 A | 9/1998 | Virnich et al. |
| 5,810,884 A | 9/1998 | Kim |
| 5,820,631 A | 10/1998 | Nobles |
| 5,830,130 A | 11/1998 | Janzen et al. |
| 5,830,232 A | 11/1998 | Hasson |
| 5,843,124 A | 12/1998 | Hammerslag |
| 5,853,421 A | 12/1998 | Leschinsky et al. |
| 5,868,778 A | 2/1999 | Gershony et al. |
| 5,871,501 A | 2/1999 | Leschinsky et al. |
| 5,906,631 A | 5/1999 | Imran |
| 5,910,155 A | 6/1999 | Ratcliff et al. |
| 5,916,236 A | 6/1999 | Muijs Van De Moer et al. |
| 5,922,009 A | 7/1999 | Epstein et al. |
| 5,928,266 A | 7/1999 | Kontos |
| 5,935,147 A | 8/1999 | Kensey et al. |
| 5,948,425 A | 9/1999 | Janzen et al. |
| 5,951,583 A | 9/1999 | Jensen et al. |
| 5,951,589 A | 9/1999 | Epstein et al. |
| 5,957,952 A | 9/1999 | Gershony et al. |
| 5,984,948 A | 11/1999 | Hasson |
| 6,007,563 A | 12/1999 | Nash et al. |
| 6,017,359 A | 1/2000 | Gershony et al. |
| 6,022,361 A | 2/2000 | Epstein et al. |
| 6,033,401 A | 3/2000 | Edwards et al. |
| 6,045,570 A | 4/2000 | Epstein et al. |
| 6,048,357 A | 4/2000 | Kontos |
| 6,048,358 A | 4/2000 | Barak |
| 6,056,768 A | 5/2000 | Cates et al. |
| 6,056,769 A | 5/2000 | Epstein et al. |
| 6,063,061 A | 5/2000 | Wallace et al. |
| 6,063,085 A | 5/2000 | Tay et al. |
| 6,066,325 A | 5/2000 | Wallace et al. |
| 6,071,300 A | 6/2000 | Brenneman et al. |
| 6,080,183 A | 6/2000 | Tsugita et al. |
| 6,090,130 A | 7/2000 | Nash et al. |
| 6,117,145 A | 9/2000 | Wood et al. |
| 6,120,524 A | 9/2000 | Taheri |
| 6,126,675 A | 10/2000 | Shchervinsky et al. |
| 6,146,372 A | 11/2000 | Leschinsky et al. |
| 6,152,943 A | 11/2000 | Sawhney |
| 6,159,232 A | 12/2000 | Nowakowski |
| 6,162,192 A | 12/2000 | Cragg et al. |
| 6,162,240 A | 12/2000 | Cates et al. |
| 6,190,400 B1 | 2/2001 | Van De Moer et al. |
| 6,206,895 B1 | 3/2001 | Levinson |
| 6,287,322 B1 | 9/2001 | Zhu et al. |
| 6,287,323 B1 | 9/2001 | Hammerslag |
| 6,296,658 B1 | 10/2001 | Gershony et al. |
| 6,302,898 B1 | 10/2001 | Edwards et al. |
| 6,315,753 B1 | 11/2001 | Cragg et al. |
| 6,315,787 B1 | 11/2001 | Tsugita et al. |
| 6,325,789 B1 | 12/2001 | Janzen et al. |
| 6,328,757 B1 | 12/2001 | Matheny |
| 6,334,865 B1 | 1/2002 | Redmond et al. |
| 6,350,274 B1 | 2/2002 | Li |
| 6,371,974 B1 | 4/2002 | Brenneman et al. |
| 6,371,975 B2 | 4/2002 | Cruise et al. |
| 6,395,015 B1 | 5/2002 | Borst et al. |
| 6,425,911 B1 | 7/2002 | Akerfeldt et al. |
| 6,458,147 B1 | 10/2002 | Cruise et al. |
| 6,475,177 B1 | 11/2002 | Suzuki |
| 6,478,808 B2 | 11/2002 | Nowakowski |
| 6,482,179 B1 | 11/2002 | Chu et al. |
| 6,482,223 B1 | 11/2002 | Nowakowski et al. |
| 6,494,848 B1 | 12/2002 | Sommercorn et al. |
| 6,524,326 B1 | 2/2003 | Zhu |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,547,806 B1 | 4/2003 | Ding |
| 6,562,059 B2 | 5/2003 | Edwards et al. |
| 6,569,185 B2 | 5/2003 | Ungs |
| 6,592,608 B2 | 7/2003 | Fisher et al. |
| 6,610,026 B2 | 8/2003 | Cragg et al. |
| 6,613,070 B2 | 9/2003 | Redmond et al. |
| 6,623,509 B2 | 9/2003 | Ginn |
| 6,623,510 B2 | 9/2003 | Carley et al. |
| 6,632,238 B2 | 10/2003 | Ginn et al. |
| 6,656,207 B2 | 12/2003 | Epstein et al. |
| 6,663,655 B2 | 12/2003 | Ginn et al. |
| 6,669,707 B1 | 12/2003 | Swanstrom et al. |
| 6,682,489 B2 | 1/2004 | Tenerz et al. |
| 6,699,261 B1 | 3/2004 | Cates et al. |
| 6,699,262 B2 | 3/2004 | Redmond et al. |
| 6,712,837 B2 | 3/2004 | Akerfeldt et al. |
| 6,733,515 B1 | 5/2004 | Edwards et al. |
| 6,743,195 B2 | 6/2004 | Zucker |
| 6,743,248 B2 | 6/2004 | Edwards et al. |
| 6,749,621 B2 | 6/2004 | Pantages et al. |
| 6,780,197 B2 | 8/2004 | Roe et al. |
| 6,790,220 B2 | 9/2004 | Morris et al. |
| 6,814,743 B2 | 11/2004 | Chin et al. |
| 6,818,008 B1 | 11/2004 | Cates et al. |
| 6,830,756 B2 | 12/2004 | Hnojewyj |
| 6,846,319 B2 | 1/2005 | Ginn et al. |

| Patent/Pub No. | Date | Inventor |
|---|---|---|
| 6,846,321 B2 | 1/2005 | Zucker |
| 6,849,061 B2 | 2/2005 | Wagner |
| 6,863,680 B2 | 3/2005 | Ashby |
| 6,890,342 B2 | 5/2005 | Zhu et al. |
| 6,899,889 B1 | 5/2005 | Hnojewyj et al. |
| 6,929,655 B2 | 8/2005 | Egnelov et al. |
| 6,936,033 B2 | 8/2005 | McIntosh et al. |
| 6,939,363 B2 | 9/2005 | Akerfeldt |
| 6,942,674 B2 | 9/2005 | Belef et al. |
| 6,949,114 B2 | 9/2005 | Milo et al. |
| 6,964,658 B2 | 11/2005 | Ashby et al. |
| 6,964,675 B2 | 11/2005 | Zhu et al. |
| 6,969,397 B2 | 11/2005 | Ginn |
| 6,984,219 B2 | 1/2006 | Ashby et al. |
| 6,989,022 B2 | 1/2006 | Nowakowski |
| 6,994,686 B2 | 2/2006 | Cruise et al. |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,748 B2 | 4/2006 | Ashby |
| 7,029,489 B1 | 4/2006 | Ashby et al. |
| 7,044,916 B2 | 5/2006 | Tenerz et al. |
| 7,048,710 B2 | 5/2006 | Cragg et al. |
| 7,073,509 B2 | 7/2006 | Tenerz et al. |
| 7,081,125 B2 | 7/2006 | Edwards et al. |
| 7,083,635 B2 | 8/2006 | Ginn |
| 7,135,027 B2 | 11/2006 | Delmotte |
| 7,169,168 B2 | 1/2007 | Muijs Van De Moer et al. |
| 7,175,646 B2 | 2/2007 | Brenneman et al. |
| 7,192,436 B2 | 3/2007 | Sing et al. |
| 7,223,266 B2 | 5/2007 | Lindenbaum et al. |
| 7,250,057 B2 | 7/2007 | Forsberg |
| 7,279,001 B2 | 10/2007 | Addis et al. |
| 7,316,704 B2 | 1/2008 | Bagaoisan et al. |
| 7,318,933 B2 | 1/2008 | Hnojewyj |
| 7,320,692 B1 | 1/2008 | Bender et al. |
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,351,249 B2 | 4/2008 | Hnojewyj et al. |
| 7,361,183 B2 | 4/2008 | Ginn |
| 7,488,340 B2 | 2/2009 | Kauphusman et al. |
| 7,553,319 B2 | 6/2009 | Bagaoisan et al. |
| RE40,863 E | 7/2009 | Tay et al. |
| 7,572,274 B2 | 8/2009 | Yassinzadeh |
| 7,597,705 B2 | 10/2009 | Forsberg et al. |
| 7,604,626 B2 | 10/2009 | McIntosh et al. |
| 7,611,479 B2 | 11/2009 | Cragg et al. |
| 7,618,436 B2 | 11/2009 | Forsberg |
| 7,621,936 B2 | 11/2009 | Cragg et al. |
| 7,625,352 B1 | 12/2009 | Ashby et al. |
| 2002/0161399 A1 | 10/2002 | Cruise et al. |
| 2003/0050664 A1 | 3/2003 | Solem |
| 2003/0051735 A1 | 3/2003 | Pavcnik et al. |
| 2003/0069601 A1 | 4/2003 | Nowakowski et al. |
| 2003/0109820 A1 | 6/2003 | Gross et al. |
| 2003/0109866 A1 | 6/2003 | Edwards et al. |
| 2003/0125766 A1 | 7/2003 | Ding |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0158573 A1 | 8/2003 | Gittings et al. |
| 2003/0191496 A1 | 10/2003 | Edwards et al. |
| 2003/0195561 A1 | 10/2003 | Carley et al. |
| 2004/0073255 A1 | 4/2004 | Ginn et al. |
| 2004/0093025 A1 | 5/2004 | Egnelov |
| 2004/0093027 A1 | 5/2004 | Fabisiak et al. |
| 2004/0122350 A1 | 6/2004 | Zhong et al. |
| 2004/0127940 A1 | 7/2004 | Ginn et al. |
| 2004/0162578 A1 | 8/2004 | Redmond et al. |
| 2004/0167570 A1 | 8/2004 | Pantages et al. |
| 2004/0176798 A1 | 9/2004 | Epstein et al. |
| 2004/0176801 A1 | 9/2004 | Edwards et al. |
| 2004/0215231 A1 | 10/2004 | Fortune et al. |
| 2004/0267308 A1 | 12/2004 | Bagaoisan et al. |
| 2005/0065549 A1 | 3/2005 | Cates et al. |
| 2005/0080452 A1 | 4/2005 | Akerfeldt |
| 2005/0085851 A1 | 4/2005 | Fiehler et al. |
| 2005/0085852 A1 | 4/2005 | Ditter |
| 2005/0085853 A1 | 4/2005 | Forsberg et al. |
| 2005/0085854 A1 | 4/2005 | Ginn |
| 2005/0107826 A1 | 5/2005 | Zhu et al. |
| 2005/0149116 A1 | 7/2005 | Edwards et al. |
| 2005/0149117 A1 | 7/2005 | Khosravi et al. |
| 2005/0245876 A1 | 11/2005 | Khosravi et al. |
| 2005/0267522 A1 | 12/2005 | Yassinzadeh et al. |
| 2006/0004408 A1 | 1/2006 | Morris et al. |
| 2006/0025815 A1 | 2/2006 | McGurk et al. |
| 2006/0034930 A1 | 2/2006 | Khosravi et al. |
| 2006/0047313 A1 | 3/2006 | Khanna et al. |
| 2006/0088570 A1 | 4/2006 | Cruise et al. |
| 2006/0100664 A1 | 5/2006 | Pai et al. |
| 2006/0161110 A1 | 7/2006 | Lenker et al. |
| 2006/0229670 A1 | 10/2006 | Bates |
| 2006/0253072 A1 | 11/2006 | Pai et al. |
| 2006/0254603 A1 | 11/2006 | Edwards et al. |
| 2006/0276838 A1 | 12/2006 | Wensel et al. |
| 2006/0276840 A1 | 12/2006 | Perper et al. |
| 2007/0032824 A1 | 2/2007 | Terwey |
| 2007/0123817 A1 | 5/2007 | Khosravi et al. |
| 2007/0135837 A1 | 6/2007 | Yassinzadeh |
| 2007/0149999 A1 | 6/2007 | Szabo et al. |
| 2007/0156084 A1 | 7/2007 | Belhe et al. |
| 2007/0213683 A1 | 9/2007 | Cassingham et al. |
| 2007/0255314 A1 | 11/2007 | Forsberg |
| 2007/0270904 A1 | 11/2007 | Ginn |
| 2007/0276433 A1 | 11/2007 | Huss |
| 2007/0276435 A1 | 11/2007 | Yassinzadeh et al. |
| 2007/0282373 A1 | 12/2007 | Ashby et al. |
| 2008/0009794 A1 | 1/2008 | Bagaoisan et al. |
| 2008/0038313 A1 | 2/2008 | Addis et al. |
| 2008/0046005 A1 | 2/2008 | Lenker et al. |
| 2008/0058862 A1 | 3/2008 | Khosravi et al. |
| 2008/0058864 A1 | 3/2008 | Bagaoisan et al. |
| 2008/0065150 A1 | 3/2008 | Drasler et al. |
| 2008/0077178 A1 | 3/2008 | Janzen et al. |
| 2008/0077179 A1 | 3/2008 | Edwards et al. |
| 2008/0082122 A1 | 4/2008 | Khosravi et al. |
| 2008/0082123 A1 | 4/2008 | Forsberg et al. |
| 2008/0097386 A1 | 4/2008 | Osypka |
| 2008/0097521 A1 | 4/2008 | Khosravi et al. |
| 2008/0108577 A1 | 5/2008 | Hnojewyj |
| 2008/0140114 A1 | 6/2008 | Edwards et al. |
| 2008/0154303 A1 | 6/2008 | Yassinzadeh |
| 2008/0161849 A1 | 7/2008 | Cates et al. |
| 2008/1017730 | 7/2008 | Mas et al. |
| 2008/0221615 A1 | 9/2008 | Ginn et al. |
| 2008/0312683 A1 | 12/2008 | Drasler et al. |
| 2008/0312684 A1 | 12/2008 | Drasler et al. |
| 2008/0319475 A1 | 12/2008 | Clark et al. |
| 2009/0054926 A1 | 2/2009 | Pipenhagen et al. |
| 2009/0062846 A1 | 3/2009 | Ken |
| 2009/0062847 A1 | 3/2009 | Ken |
| 2009/0062848 A1 | 3/2009 | Ken |
| 2009/0082802 A1 | 3/2009 | Benjamin et al. |
| 2009/0088793 A1 | 4/2009 | Bagaoisan et al. |
| 2009/0088794 A1 | 4/2009 | LaFontaine |
| 2009/0112182 A1 | 4/2009 | Razavi |
| 2009/0112257 A1 | 4/2009 | Preinitz et al. |
| 2009/0125056 A1 | 5/2009 | Buchbinder et al. |
| 2009/0143815 A1 | 6/2009 | Eidenschink et al. |
| 2009/0143817 A1 | 6/2009 | Akerfeldt |
| 2009/0171387 A1 | 7/2009 | Pipenhagen et al. |
| 2009/0177225 A1 | 7/2009 | Nunez et al. |
| 2009/0216267 A1 | 8/2009 | Willard et al. |
| 2009/0222037 A1 | 9/2009 | Babaev et al. |
| 2009/0228039 A1 | 9/2009 | Babaev et al. |
| 2009/0254110 A1 | 10/2009 | Bagaoisan et al. |
| 2009/0275978 A1 | 11/2009 | Yassinzadeh |
| 2009/0312790 A1 | 12/2009 | Forsberg et al. |
| 2009/0318955 A1 | 12/2009 | Dave et al. |
| 2010/0023051 A1 | 1/2010 | White et al. |

* cited by examiner

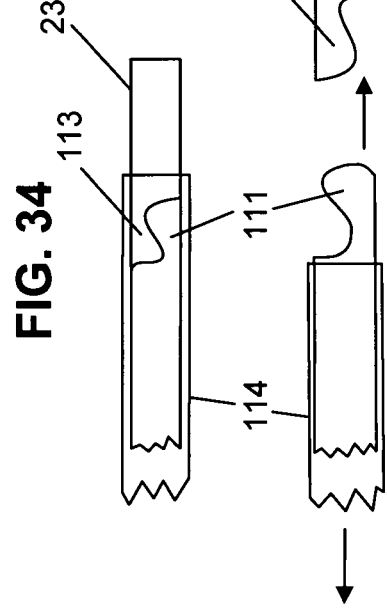
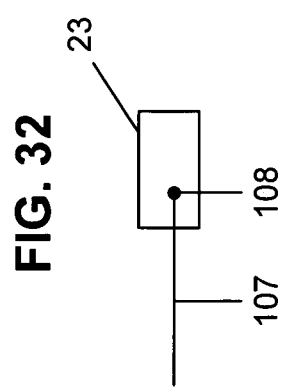
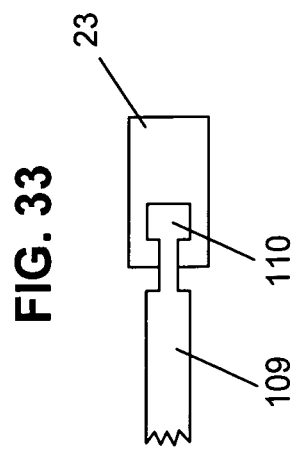

METHOD AND SYSTEM FOR SEALING PERCUTANEOUS PUNCTURES

This application claims the benefit of priority from U.S. Provisional Application No. 61/190,085, filed Aug. 26, 2008, U.S. Provisional Application No. 61/213,407, filed Jun. 4, 2009, and PCT Application No. PCT/US09/54492, filed Aug. 20, 2009, each of which is herein incorporated by reference in its entirety.

FIELD OF THE INVENTION

The present disclosure relates generally to a method and system for sealing, and more particularly, to a method and system for sealing percutaneous punctures.

BACKGROUND OF THE INVENTION

The invention relates generally to the sealing of punctures for various medical procedures and more particularly to the sealing of such punctures using, in certain embodiments, a multi-stage sealing material ejected into the puncture.

Certain medical procedures require the percutaneous puncturing of the body tissue of a patient to gain access to a cavity in the body to perform a medical procedure. One example of such a procedure is the puncturing of body tissue and a blood vessel wall to gain access to the interior of the vascular system of the patient. Such procedures that commonly require the percutaneous puncturing of a blood vessel wall are balloon angioplasty procedures, arteriography, venography, angiography and other diagnostic procedures that use blood vessel catheterization. Examples of other procedures requiring a puncture through body tissue into a cavity include laparoscopic surgery and other microscopic surgery techniques using a small incision.

In each of these procedures, it is necessary to close the incision or puncture through the body tissue after the surgical procedure. While there are a variety of prior art devices and techniques for closing such punctures, one of the primary problems associated with the prior art is ensuring a complete seal of the puncture. The invention described herein provides an improvement over the prior art by resolving this problem and other problems.

SUMMARY OF THE INVENTION

In one aspect, the present disclosure is directed to a device for sealing a puncture in a patient. The device includes a sealing component including an elongate control member configured to pass through a puncture in skin of a patient. The sealing component also includes an expandable member disposed near a distal end of the elongate control member, and a tip releasably attached to the elongate control member distal to the expandable member. The device also includes a sealing material delivery component including a delivery tube through which the elongate control member of the sealing component is configured to extend. The delivery tube is configured to deliver sealing material through an opening in a distal end of the delivery tube.

In another aspect, the present disclosure is directed to a method of sealing a puncture in a wall of a body cavity of a patient. The method includes inserting a sealing component and a sealing material delivery component through a puncture in a wall of a body cavity of a patient. The sealing material delivery component includes a delivery tube, and the sealing component is slidably disposed in the delivery tube and includes an elongate control member. The method also includes inserting an expandable member connected to the elongate control member through the puncture into the body cavity, expanding the expandable member when the expandable member is distal to a distal end of the delivery tube and inserted in the body cavity, and moving the expandable member near a distal surface of the wall of the body cavity. The method further includes delivering a first sealing material through the distal end of the delivery tube and into the puncture, withdrawing the elongate control member from the patient, and delivering a second sealing material proximal to the wall of the body cavity after the elongate control member is withdrawn from the patient.

In a further aspect, the present disclosure is directed to a method of sealing a puncture in a wall of a body cavity of a patient. The method includes inserting a sealing component and a sealing material delivery component through a puncture in a wall of a body cavity of a patient. The sealing material delivery component includes a delivery tube, and the sealing component is slidably disposed in the delivery tube and includes an elongate control member. The method also includes inserting an expandable member connected to the elongate control member through the puncture into the body cavity, expanding the expandable member when the expandable member is distal to a distal end of the delivery tube and inserted in the body cavity, and moving the expandable member near a distal surface of the wall of the body cavity. The method further includes delivering sealing material through the distal end of the delivery tube and into the puncture, inserting a tip disposed on the elongate control member and distal to the expandable member into the sealing material, and detaching the tip from the elongate control member when the tip is in the sealing material.

In yet another aspect, the present disclosure is directed to a method of sealing a puncture in a wall of a body cavity of a patient. The method includes inserting a sealing component and a sealing material delivery component through a puncture in a wall of a body cavity of a patient. The sealing material delivery component includes a delivery tube, and the sealing component is slidably disposed in the delivery tube and includes an elongate control member. The method also includes inserting an expandable member on the elongate control member through the puncture into the body cavity, and expanding the expandable member when the expandable member is distal to a distal end of the delivery tube and inserted in the body cavity. The method further includes locating the wall of the body cavity by retracting the sealing component with respect to the patient until the expandable member in the expanded configuration abuts a distal surface of the wall of the body cavity, and delivering sealing material through the distal end of the delivery tube and proximal to the wall of the body cavity.

In yet a further aspect, the present disclosure is directed to a sealing component for sealing a puncture in a patient. The sealing component includes an elongate control member configured to pass through a puncture in skin of a patient, an expandable member disposed near a distal end of the elongate control member, and a tip releasably attached to the elongate control member distal to the expandable member.

In yet another aspect, the present disclosure is directed to a method of sealing a puncture in a wall of a body cavity of a patient. The method includes inserting a sealing component and a sealing material delivery component through a puncture in a wall of a body cavity of a patient. The sealing material delivery component includes a delivery tube, and the sealing component is slidably disposed in the delivery tube and includes an elongate control member. The method also includes inserting an expandable member releasably connected to the elongate control member through the puncture into the body cavity, expanding the expandable member when the expandable member is distal to a distal end of the delivery tube and inserted in the body cavity, and moving the expandable member near a distal surface of the wall of the body cavity. The method further includes delivering a sealing material through the distal end of the delivery tube and into the puncture, collapsing the expandable member, and inserting the collapsed expandable member in a cavity formed in the sealing material. The method also includes expanding the expandable member in the cavity formed in the sealing material and detaching the expandable member in the expanded configuration from the elongate control member when the expandable member is in the sealing material.

BRIEF DESCRIPTION OF THE DRAWINGS

FIGS. 32-35 illustrate various exemplary embodiments of mechanisms for releasably attaching a tip to a temporary sealing component.

These figures and the following detailed description disclose specific embodiments of the invention, however, it is to be understood that the inventive concept is not limited thereto and may be embodied in other forms.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The systems disclosed herein can be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal the percutaneous punctures made to gain access to blood vessels in patients for various procedures. It will be appreciated that the systems are applicable to other procedures requiring sealing of a puncture through body tissue into a cavity including laparoscopic surgery and other microscopic surgery techniques using a small incision.

The terms proximal and distal are used herein to refer to the relative positions of the components of the exemplary sealing system 10. When used herein, proximal refers to a position relatively closer to the exterior of the body or closer to the surgeon using the sealing system 10. In contrast, distal refers to a position relatively further away from the surgeon using the sealing system 10 or closer to the interior of the body.

Figure 3:
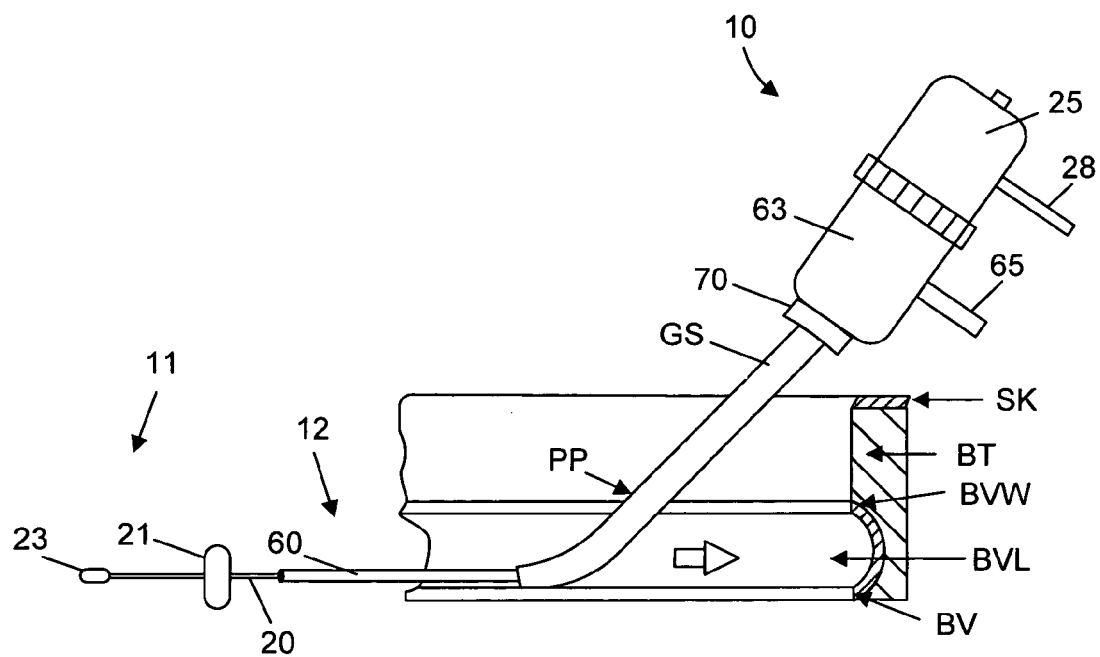
FIG. 3 illustrates an exemplary embodiment with the sealing system assembled and inserted into a guide sheath protruding from a blood vessel.

An exemplary embodiment of sealing system 10 is illustrated being used to seal a percutaneous puncture PP seen in FIG. 3 made through the skin SK, body tissue BT and the wall BVW of a blood vessel BV as an incident to a medical procedure. Typically, the blood vessel BV used is a femoral artery in the groin region with a relatively large vessel passage or lumen BVL to facilitate locating the blood vessel BV and permitting a sufficiently large puncture to be made through the wall BVW thereof to carry out the procedure. Medical procedures which are typically performed through such a puncture are angioplasty and other procedures which pass a catheter or other type of probe into and along the blood vessel lumen BVL. When such a procedure is performed, an initial percutaneous puncture PP with an appropriate needle is made from the patient's skin SK through the tissue BT and the blood vessel wall BVW into the blood vessel lumen BVL, and a guide wire is installed. The needle is then removed leaving the guide wire in place and a tapered introducer guide sheath GS is installed over the guide wire to enlarge the puncture so as to permit easier access to the blood vessel BV. The guide sheath GS serves to keep the passage open and prevent further damage to the tissue BT and skin SK around the passage during the medical procedure. The guide sheath GS, while not required to be used in connection with the present invention, assists in the installation of the sealing system 10 as will become more apparent.

Figure 1:
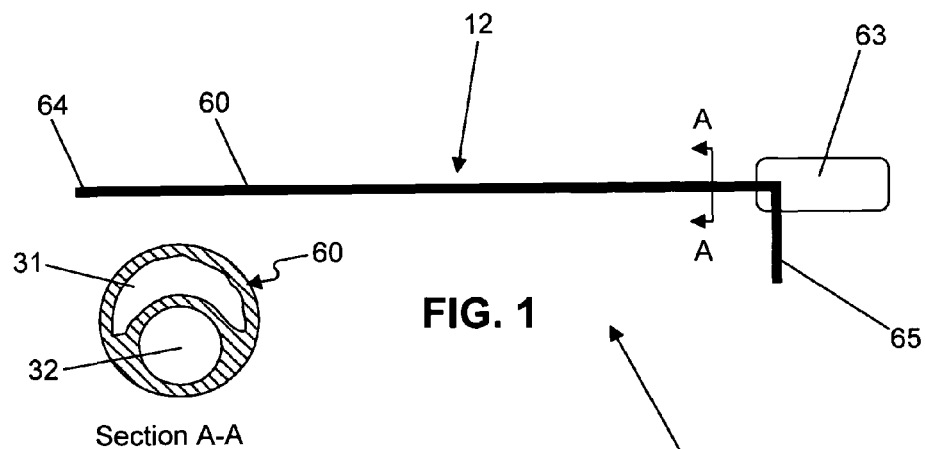
FIG. 1 is a side view of an exemplary embodiment showing a delivery component.
Figure 2:
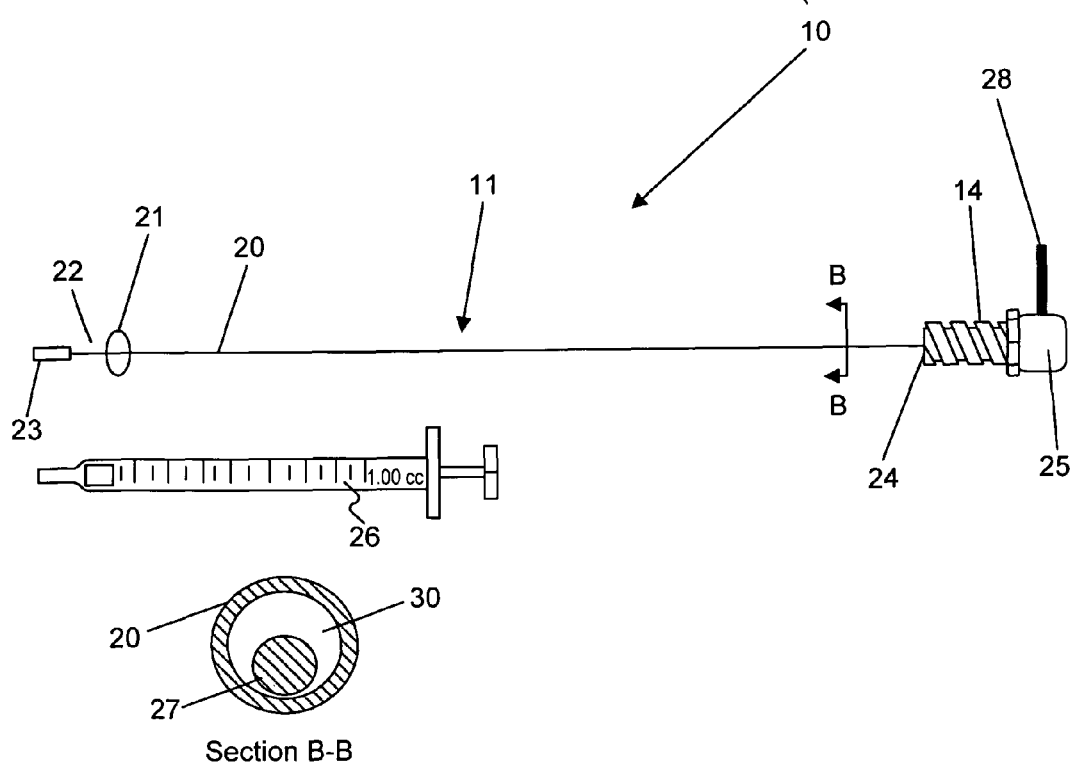
FIG. 2 is a side view of an exemplary embodiment showing a temporary sealing component.

Referring to FIGS. 1 and 2, an exemplary embodiment of the sealing system 10 is illustrated showing a temporary sealing component 11 and a sealing material delivery component 12. The connector 14 permits positioning of the temporary sealing component 11 relative to the sealing material delivery component 12 in one or more defined positions relative to each other and allows one to positively locate the temporary sealing component 11 and the sealing material delivery component 12 when inserted into the puncture PP. The temporary sealing component 11 typically may be pre-assembled within the sealing material delivery component 12 during manufacture, creating the sealing system 10.

Figure 4:
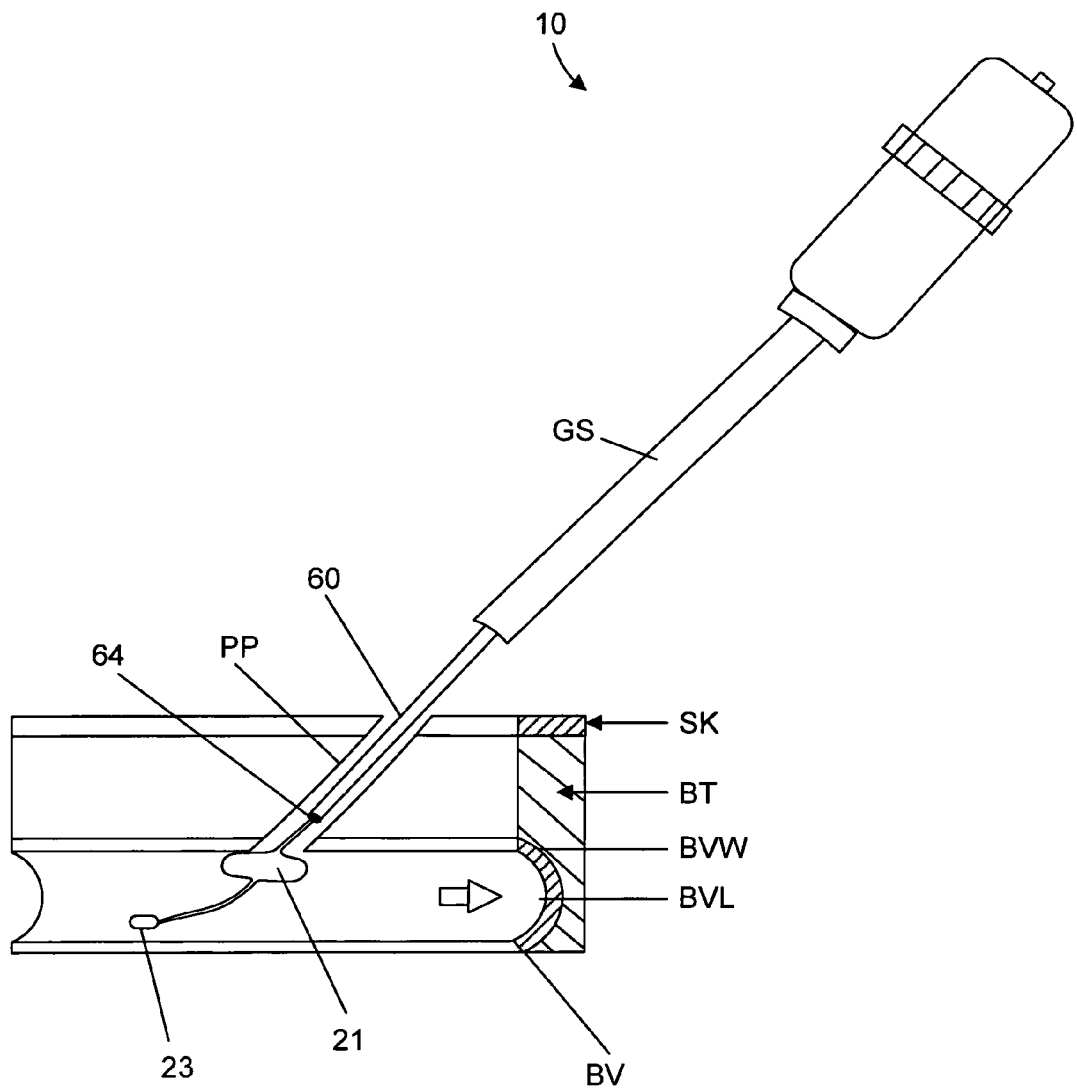
FIG. 4 illustrates an exemplary embodiment with the guide sheath and the assembled sealing system in a retracted position.
Figure 5:
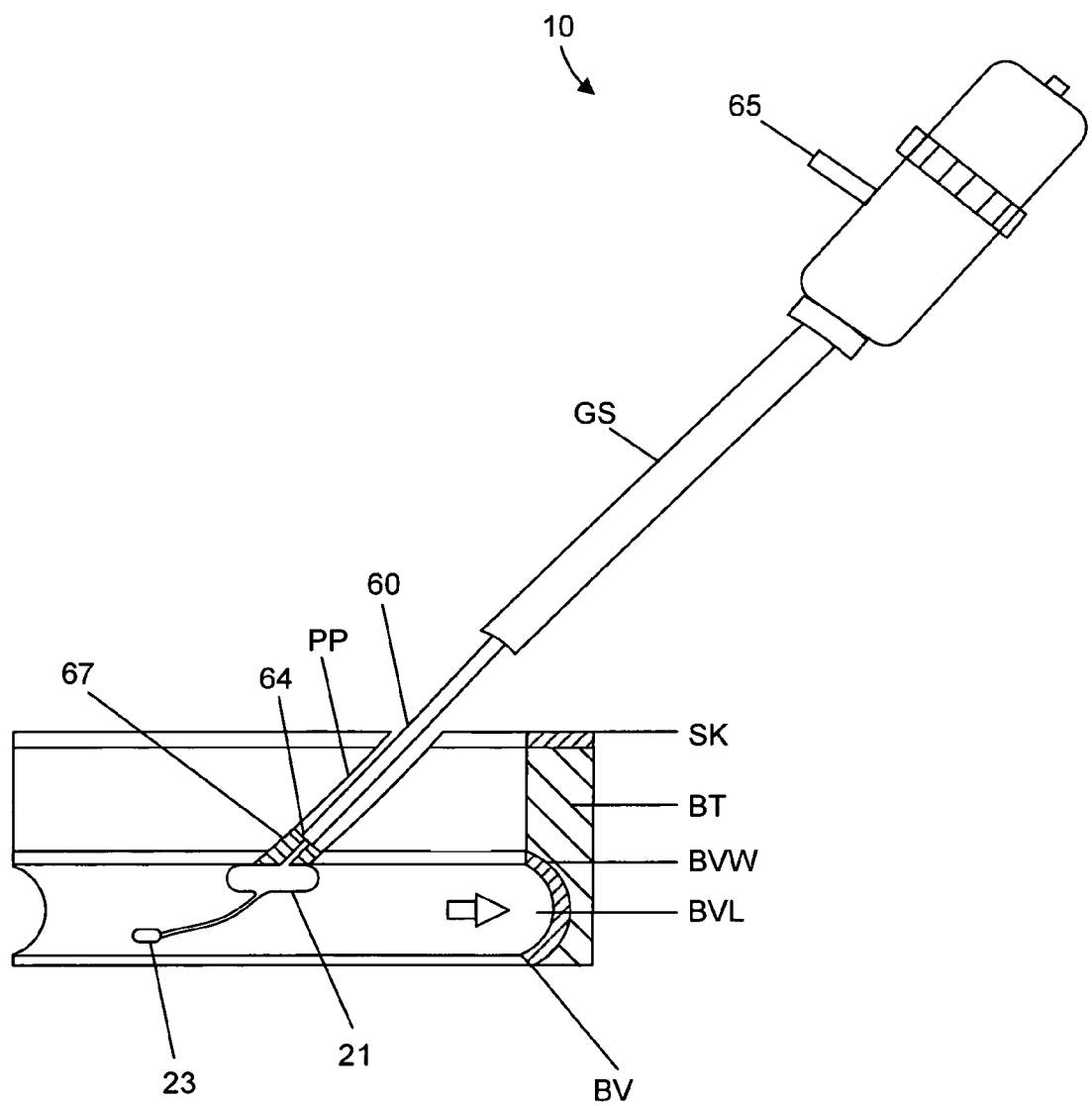
FIG. 5 illustrates an exemplary embodiment with the sealing system delivering the first stage of sealing material into the puncture.
Figure 6:
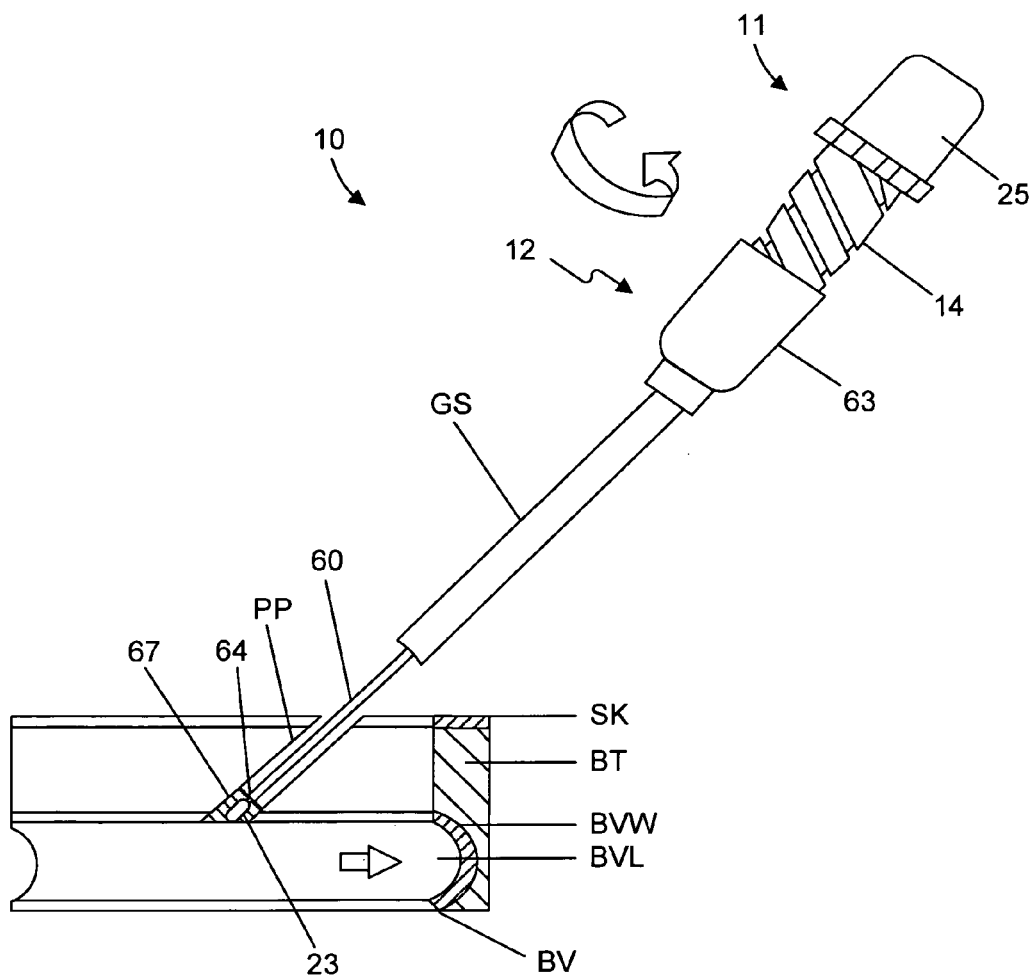
FIG. 6 illustrates an exemplary embodiment with the temporary sealing component being removed from the assembled sealing system.
Figure 7:
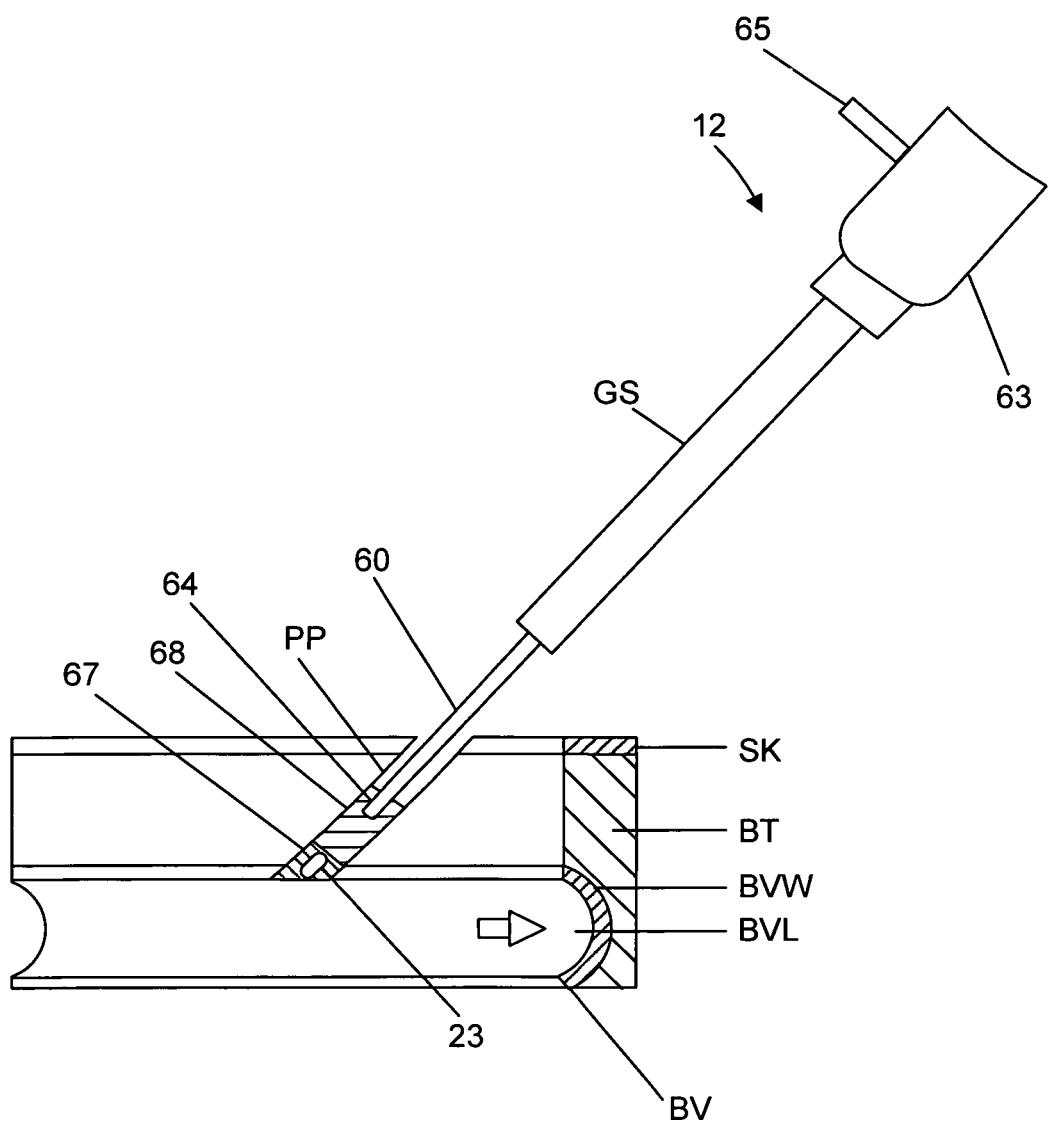
FIG. 7 illustrates an exemplary embodiment with the delivery component delivering the second stage of sealing material into the puncture.

The sealing system 10 is inserted into the blood vessel lumen BVL through the introducer guide sheath GS as seen in FIG. 3. As described in greater detail below, an expandable tamponading member 21 of temporary sealing component 11 is expanded. The sealing system 10 and sheath GS are then retracted, and the expandable tamponading member 21 of temporary sealing component 11 serves to temporarily seal the interior end of the puncture PP opening into the blood vessel lumen BVL. While the temporary sealing component 11 is in the proper retracted position for sealing the puncture PP in the blood vessel BV, the sealing material delivery component 12 is located in the puncture PP and proximate to the punctured blood vessel wall BVW, as seen in FIG. 4. When the sealing material delivery component 12 is located proximate to the punctured blood vessel wall BVW, the first stage 67 of the sealing material for sealing the puncture PP is injected through the sealing material delivery component 12 as seen in FIG. 5 and as described in greater detail below. After the first stage 67 of sealing material is installed, the expandable tamponading member 21 is contracted and temporary sealing component 11 is removed, leaving a bioabsorbable tip 23 behind as seen in FIG. 6. A second stage 68 of sealing material is then installed in the puncture PP as the sealing material delivery arrangement 12 is removed as seen in FIG. 7.

Referring further to FIG. 1, the exemplary embodiment of the sealing material delivery component 12 comprises a distal end 64, a delivery tube 60, a first coupling 63, and a first sealing material port 65. In alternate embodiments of the present invention there may be multiple sealing material ports. The distal end 64 is the opening through which the first and second stage sealing materials 67, 68 are deposited into the puncture PP. The delivery tube 60 may be manufactured from any number of materials without departing from the scope of the invention. In an embodiment, the delivery tube 60 is made of a polymeric material such as high-density polyethylene (HDPE) or polyamide.

FIG. 1 also illustrates an exemplary cross section of delivery tube 60 showing a double-barrel tube with cavities 31 and 32. The shape of cavities 31 and 32 can take a variety of forms. Cavity 31 is the cavity through which the sealing material (first stage 67 and/or second stage 68) passes on its way to exiting at the distal end 64 and being deposited in the puncture PP. In alternate embodiments of the invention, cavity 31 may be divided into two or more cavities, where a different stage 67, 68 of sealing material passes through each distinct cavity. Cavity 32 is the space through which the temporary sealing component 11 passes when the sealing system 10 is assembled. Cavity 32 also may be used for delivery of sealing material, and particularly second stage sealing material 68, when temporary sealing component 11 is removed from cavity 32.

The sealing material used in the first and second stages 67, 68 of sealing the puncture PP may be any of a number of different biocompatible materials as long as the material has the capability of maintaining a seal in the puncture PP. For example, the sealing material could be a liquid or gel that is flowable. The sealing material can be a combination of liquid and solid materials, for example, the first stage sealing material 67 could be a preformed solid and the second stage sealing material 68 could be a flowable material. In yet another embodiment, the sealing material can be a compound that is mixed either prior to inserting the sealing material into the sealing material delivery component 12 or that is mixed as it passes through the sealing material delivery component 12. The sealing material may be a material that actually bonds the body tissue BT at the puncture PP together such as a biocompatible adhesive. In an embodiment described herein, the sealing material is a polyethylene glycol based adhesive in a flowable state.

The exemplary temporary sealing component 11 illustrated in FIG. 2 fits within cavity 32 of sealing material delivery component 12 so that the two components can be assembled into the sealing system 10. The temporary sealing component 11 includes an elongate flexible control member 20. Proximate to the distal end of the control member 20 is mounted an expandable tamponading member 21. In addition to serving a tamponading function, expandable member 21 also provides a locating function as described in connection with FIG. 4 below. The control member 20 is configured so that the distal end 22 and bioabsorbable tip 23 may pass through the guide sheath GS into the blood vessel lumen BVL. The proximal end 24 of member 20 connects with a second coupling 25 which includes an expansion mechanism. The expansion mechanism controls the expansion and contraction of the expandable tamponading member 21. The expansion mechanism may take a variety of forms including a tube for delivery of an expansion gas or liquid or springs, couplings or other mechanical or electromechanical components for adjusting the size of the expandable tamponading member 21. In an embodiment, second coupling 25 includes a port or valve 28 for connection to a syringe 26. The port 28 is connected to the proximal end 24 of control member 20 and allows a gas or liquid from the syringe 26 to expand and contract the expandable tamponading member 21. In its collapsed condition, the expandable tamponading member 21 closely adheres to the outside surface of control member 20. In its expanded condition, the expandable tamponading member 21 is large enough to seal the puncture PP in the body cavity as illustrated in FIG. 4 and as described further below.

Second coupling 25 also includes a connector 14 to fix the position of the temporary sealing component 11 to first coupling 63 of the sealing material delivery component 12. The connector 14 is illustrated as a threaded member in the exemplary embodiment shown in FIG. 2. However, connector 14 can take a variety of forms and may be attached to first coupling 63 through a variety of attaching mechanisms including springs, clips and various recesses or protrusions.

The exemplary embodiment shown in FIG. 2 also illustrates a cross section of control member 20 showing inflation lumen 30 and wire 27. The inflation lumen 30 is the cavity through which the liquid or gas passes to expand and contract the expandable tamponading member 21. The wire 27 connects second coupling 25 to the proximal end of bioabsorbable tip 23. As explained further below, the bioabsorbable tip 23 may be detached from the wire 27 and deposited in the puncture PP to assist with sealing the puncture PP. The bioabsorbable tip 23 can be made from a variety of materials including polyethylene glycol, polylactic acid, collagen, a bioadhesive glue, or a combination of these or other bioabsorbable materials. It is understood that tip 23 alternatively may be any biocompatible material that is not bioabsorbable, but instead suitable for implantation in the body. Such a tip may be either removed later or remain in the body.

It will be appreciated that the tamponading member 21 may be mechanically, electrically, pneumatically or hydraulically expanded and collapsed without departing from the scope of the invention. The particular expanded exterior configuration of the tamponading member 21 can be selected depending on the particular circumstances of use. The criteria that is used to determine the particular size and configuration is the blood vessel condition at the puncture PP and the cross-sectional size and shape of the blood vessel lumen BVL in the vicinity of the puncture PP. The largest cross-sectional dimension of the expanded tamponading member 21 may be small enough for the member 21 to be pulled back against the interior end of the puncture PP without dragging or hanging up in the blood vessel lumen BVL. It has been found that an expanded dimension in one direction for the member 21 that is at least about 1.5 times larger than the puncture PP is satisfactory to prevent the tamponading member 21 from being pulled back through the puncture PP under typical conditions.

One function of the tamponading member 21 is to seal the body cavity so that fluid does not leak from the cavity in the puncture PP. To achieve a seal, in an exemplary embodiment, the portion of the tamponading member 21 near the puncture PP may be larger in cross-sectional area than the cross-sectional area of the puncture PP to insure sealing when the tamponading member 21 is pulled back up against the interior end of the puncture PP. While different expanded sizes may be used, dimensions on the order of 0.150-0.200 inch (3.8-5.1 mm) may be successful under typical conditions where the puncture PP is made with a 4 french needle.

Another function of the tamponading member 21 is to positively locate the interior surface of the body cavity. Once the temporary sealing component 11 is retracted so that the tamponading member 21 is pulled back against the inside wall of the body cavity, this may allow the surgeon to know the location of the body cavity wall and to properly position the sealing material delivery component 12.

Without limiting the scope of the invention, the particular temporary sealing component 11 illustrated may be a balloon catheter with the tamponading member 21 illustrated in FIG. 2 as a small inflatable balloon which can be inflated. In the expanded condition, the tamponading member 21 has a puncture facing surface formed at the radius between the tamponading member 21 and control member 20 that serves to substantially center the control member 20 in the end of the puncture PP and maintain the end of the puncture PP closed. This is because the tamponading member 21 may shift in the end of the puncture PP until the force exerted on the tamponading member 21 by the blood vessel wall BVW and the body tissue BT is equally distributed around the control member 20. The tamponading member 21 is inflated and deflated through the control member 20 as will become more apparent. The inflatable tamponading member 21 may be made out of any suitable material such as latex. In alternate embodiments where the tamponading member 21 is mechanically expanded, it may be made of a metallic mesh which may or may not include a flexible covering.

The control member 20 is a thin elongate flexible member considerably smaller than the puncture PP. The diameter of the control member 20 may be about 0.03 inch in procedures involving the femoral artery. The control member 20 is sufficiently long to extend from within the blood vessel lumen BVL out through the puncture PP exteriorly of the patient so that it can be manually manipulated. To permit the tamponading member 21 to be inflated, the control member 20 defines an inflation lumen 30 therethrough that extends from the valve 28, through second coupling 25, and to the interior of the tamponading member 21 along the length of the control member 20. Thus, the tamponading member 21 can be inflated and deflated through the lumen 30 from a position external of the patient.

The tamponading member 21 can be expanded and contracted by any of a variety of mechanical, electromechanical, pneumatic, or hydraulic techniques. As illustrated in the exemplary embodiment shown in FIG. 2, the tamponading member 21 is inflated by any convenient fluid inflation device such as syringe 26. The syringe 26 or other inflation device may be of the same type as that already used in balloon angioplasty and is connected to the exterior end of the control member 20 through valve 28 used to selectively seal the inflation lumen 30. The inflation fluid under pressure from the syringe 26 flows along the inflation lumen 30 in the control member 20 into the tamponading member 21 to selectively inflate same. The syringe 26 also is used to collapse the tamponading member 21 when it is to be withdrawn as described further below.

Referring to FIG. 3, an exemplary embodiment of the sealing system 10 is illustrated as inserted through a guide sheath GS. Typically the guide sheath GS may be in place in puncture PP in connection with a surgical procedure. While the exemplary embodiment shown in FIG. 3 involves inserting the sealing system 10 through a guide sheath GS, the guide sheath GS is not required for use with the sealing system 10. When the surgical procedure is completed, the sealing system 10 can be inserted through guide sheath GS until delivery tube 60, control member 20, tamponading member 21, and bioabsorbable tip 23 are positioned within the blood vessel BV.

The exemplary embodiment shown in FIG. 3 illustrates the first coupling 63 up against the hub 70 of the guide sheath GS. In certain embodiments, the first coupling 63 of sealing system 10 may be attached to the hub 70 of guide sheath GS. Such an attaching feature can be useful for fixing the position of the sealing system 10 relative to the guide sheath GS. The first coupling 63 may be attached to the hub 70 of guide sheath GS through a variety of mechanisms including threads, clips, snaps, protrusions, or recesses.

Once the tamponading member 21 is within the blood vessel BV, it can be inflated so that its cross-sectional area is larger than the cross-sectional area of the puncture PP. While not shown in FIG. 3, the tamponading member 21 is inflated using an expanding mechanism such as syringe 26 shown in FIG. 2. In this exemplary embodiment, the syringe 26 is coupled to valve 28 and a fluid or gas is pushed from the syringe 26, through the inflation lumen 30 in control member 20, and into the tamponading member 21.

Referring to FIG. 4, an exemplary embodiment of sealing system 10 is illustrated with the sealing system 10 in a retracted position. In the embodiment shown in FIG. 4, both the sealing system 10 and the guide sheath GS have been retracted so that tamponading member 21 has been pulled up against the puncture PP in the blood vessel wall BVW. Because the tamponading member 21 has been inflated to a cross-sectional size greater that the cross-sectional size of the puncture PP, the tamponading member 21 remains up against the blood vessel wall BVW and may not pass into the puncture PP.

Retracting the exemplary sealing system 10 as shown in FIG. 4 allows the surgeon to create a seal with the tamponading member 21 pulled up against the interior of the blood vessel wall BVW. Creating a seal in the puncture PP prevents blood from flowing up into the puncture and creates a relatively dry environment in the puncture PP in preparation for depositing sealing material into the puncture PP. The surgeon may also confirm that the puncture PP in the blood vessel wall BVW is sealed by using a syringe to draw a vacuum through cavity 31 in delivery tube 60. If the syringe draws blood from the puncture PP through the cavity 31, this may indicate to the surgeon that the puncture PP is not properly sealed at the blood vessel wall BVW.

Retracting the sealing system 10 so that the tamponading member 21 is pulled up against the interior of the blood vessel wall BVW also allows the surgeon to confirm the location of the sealing system 10 and the delivery tube 60 within the puncture PP. In certain embodiments, the surgeon may install a clip onto the shaft of delivery tube 60 to mark where the delivery tube 60 exits the skin SK. This mark on the delivery tube 60 may serve to positively locate the distal end 64 of delivery tube 60 with respect to the blood vessel wall BVW, even after the tamponading member 21 is contracted and withdrawn as described below.

In the retracted position illustrated in FIG. 4, the delivery tube 60 of the sealing material delivery component 12 has been retracted to a position where its distal end 64 is located within the puncture PP but proximate to the distal end of the puncture PP. The relative location of the distal end 64 of the delivery tube 60 with respect to the tamponading member 21 can be adjusted depending on the type of procedure and the patient.

Referring to FIG. 5, an exemplary embodiment of the sealing system 10 is illustrated performing the deposit of the first stage of sealing material 67 in the puncture PP. The first stage of sealing material 67 can be mixed outside of the sealing system 10, for example, in a double-barrel syringe (not shown). The mixed first stage of sealing material 67 is then injected into first sealing material port 65 and flows through cavity 31 in delivery tube 60. In alternate embodiments of the invention, the first stage sealing material 67 can be mixed in cavity 31 as it flows along the inside of the delivery tube 60. As illustrated in FIG. 5, the distal end 64 of delivery tube 60 has been positioned proximate to the blood vessel wall BVW. The first stage sealing material 67 exits the delivery tube 60 at the distal end 64 and is deposited in the region immediately proximate to the blood vessel wall BVW creating a seal where the puncture PP passed through the blood vessel wall BVW. However, as illustrated in FIG. 5, the seal created with the first stage sealing material 67 may not be a complete seal because control member 20 still passes through the first stage sealing material 67 and into the blood vessel BV.

In alternate embodiments, the first stage sealing material 67 can be a solid material with a preformed hollow center through which the control member 20 passes. The solid material with the preformed hollow center can be pushed into the puncture PP or deposited in the puncture PP by a modified version of the sealing system 10 so that the solid material is positioned proximate to the blood vessel wall BVW.

Referring to FIG. 6, the exemplary sealing system 10 is illustrated with the step of removing the temporary sealing component 11. In this step of the exemplary procedure, first the tamponading member 21 is contracted by releasing the valve 28 so that the liquid or gas can pass out of the tamponading member 21, back up the inflation lumen 30 and into the syringe 26 (not shown). Once the tamponading member 21 is contracted, the surgeon can rotate the second coupling 25 as shown in the exemplary embodiment in FIG. 6. Rotating the second coupling 25 causes the temporary sealing component 11 to retract and separate from the sealing material delivery component 12. As shown in FIG. 6, in an embodiment of the sealing system 10, the second coupling 25 is attached to the first coupling 63 using threads. The threads allow the second coupling 25 and the temporary sealing component 11 to be gently separated from the sealing material delivery component 12. In alternate embodiments of the sealing system 10, the second coupling 25 and the first coupling 63 can be connected and detached using alternate mechanisms such as clips, snaps, protrusions, or recesses.

Retracting the temporary sealing component 11 removes the contracted tamponading member 21 and the control member 20 from the blood vessel BV and through the first stage sealing material 67. However, retraction of the tamponading member 21 and the control member 20 through the first stage sealing material 67 leaves an opening in the first stage sealing material 67 called a tract (not shown). Furthermore, depending on the type of first stage sealing material 67 used, it may be difficult to retract the control member 20 from the first stage sealing material 67. Certain embodiments of the sealing system 10 may employ an additional sheath (not shown) around the control member 20 where the additional sheath is made of a material that resists adhesion to the first stage sealing material 67 and facilitates retraction of the control member 20 from the first stage sealing material 67.

Referring to the hollow passage or tract in the first stage sealing material 67, as the temporary sealing component 11 is further retracted, the bioabsorbable tip 23 may pass into the tract in the first stage sealing material 67 and serve to fill the hollow space defined by the tract. In this way the bioabsorbable tip 23 provides an improved method for completely sealing the puncture PP. A variety of mechanisms may be employed to release the bioabsorbable tip 23 from the wire 27 so that it may be deposited in the tract in the first stage sealing material 67. For example, in an embodiment, the bioabsorbable tip 23 is larger in diameter than the distal end 64 of the delivery tube 60. As the temporary sealing component 11 is retracted, the bioabsorbable tip 23 engages the distal end 64 of delivery tube 60 and with sufficient tension, the bioabsorbable tip 23 breaks off of the wire 27 and remains in the tract. In alternate embodiments of the invention, the bioabsorbable tip 23 may be released from the temporary sealing component 11 using a mechanical or electro-mechanical release mechanism. In yet other embodiments of the invention, the bioabsorbable tip 23 can be designed to fracture under a certain tension so that a portion of the bioabsorbable tip 23 breaks free of the wire 27 and is deposited in the tract.

Referring to FIG. 7, an exemplary embodiment of the sealing system 10 is illustrated with the temporary sealing component 11 having been removed as described in connection with FIG. 6. FIG. 7 illustrates the final step of the exemplary sealing process, namely, the depositing of the second stage sealing material 68 in the puncture PP. As illustrated in FIG. 7, the bioabsorbable tip 23 remains within the tract in the first stage sealing material 67 proximal to the blood vessel wall BVW. The second stage sealing material 68 can be used to fill the remainder of the puncture PP as well as to seal off any remaining gaps in and around the tract and the first stage sealing material 67. The second stage sealing material 68 may either have the same or a different composition from the first stage sealing material 67.

In an embodiment, the second stage sealing material 68 is mixed outside the sealing system 10, for example, in a double-barrel syringe, and is injected into the first sealing material port 65. However, in this embodiment the second stage sealing material 68 flows through cavity 32 because cavity 31 may be impassable because it is filled with the first stage sealing material 67 which may have set. In an embodiment, cavity 32 may have a one-way valve so that the second stage sealing material 68 passes down the cavity 32 toward the distal end 64 and not in the opposite direction and out the proximal end of first coupling 63. In one alternate embodiment of the sealing system 10, the second stage sealing material 68 is injected through a second sealing material port (not shown). In another alternate embodiment of the sealing system 10, the second stage sealing material 68 is not mixed until it passes along the cavity 32 within the delivery tube 60. In yet another alternate embodiment of the sealing system 10, there may be additional cavities along the length of delivery tube 60 permitting components of the second stage sealing material 68 to remain separate until they are deposited and mixed in the puncture PP.

As shown in FIG. 7, the second stage sealing material 68 exits the distal end 64 of delivery tube 60 and fills the remainder of the puncture PP. As the second stage sealing material 68 is deposited, the surgeon can retract the sealing material delivery component 12. The second stage sealing material 68 can be used to completely fill and seal the puncture PP.

Figure 8:
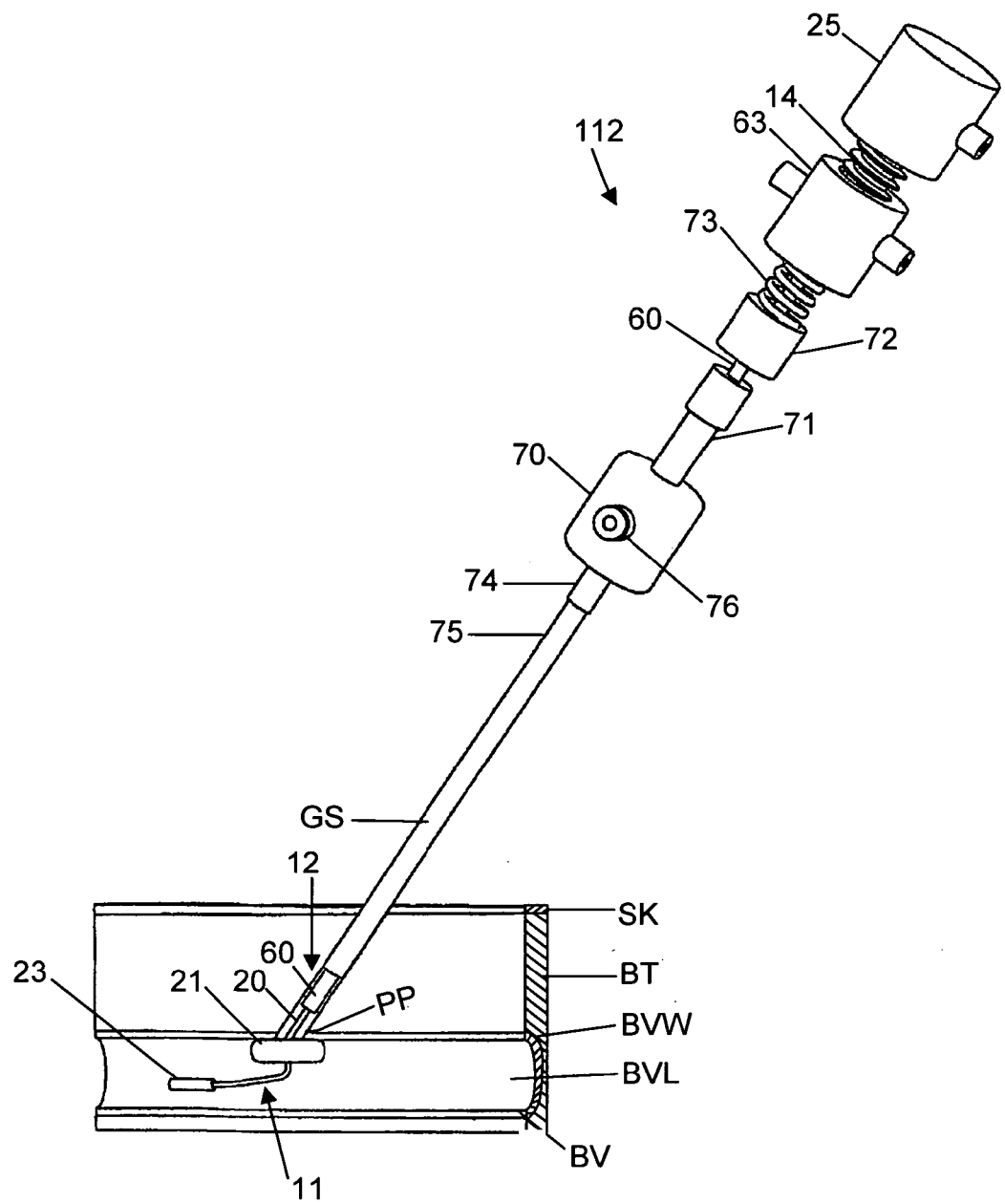
FIG. 8 illustrates an exemplary embodiment with the guide sheath remaining in tract during closure with sealing system inserted.

FIG. 8 shows an embodiment of a sealing system 112 including temporary sealing component 11. In the embodiment of the sealing system 112 shown in FIG. 8, the guide sheath GS remains through the skin SK and body tissue BT during the closure of the percutaneous puncture PP.

The exemplary embodiment shown in FIG. 8 illustrates a coupling 71 disposed up against hub 70 of the guide sheath GS. In certain embodiments, the coupling 71 of sealing system 112 may be attached to hub 70 of the guide sheath GS. Such an attaching feature can be useful for fixing the position of the sealing system 112 relative to the guide sheath GS.

An additional benefit of having guide sheath GS remain through the skin SK and body tissue BT is that the guide sheath GS seals the tract and/or acts as a cork and provides a confined space that forces the sealing material to remain within the body tissue BT.

Another benefit of having guide sheath GS remain through the skin SK and body tissue BT is the ability to aspirate any fluid that may be present within the body tissue BT tract. A syringe can be attached to luer fitting 76 to apply a vacuum and aspirate fluid from body tissue BT.

A benefit of aspirating any fluid or blood from tract puncture PP is the ability to verify that the tamponading member 21 has been pulled up against blood vessel wall BVW and has sealed the puncture PP.

Coupling 71 may be attached to hub 70 with a variety of means and at a variety of locations. For example, coupling 71 may be attached to the outside or inside of hub 70, to proximal or distal ends of hub 70, or onto the shaft 74, 75 of guide sheath GS. The coupling 71 may be attached to the hub 70 of the guide sheath GS through a variety of mechanisms including threads, clips, snaps, protrusions or recesses.

Figure 9:
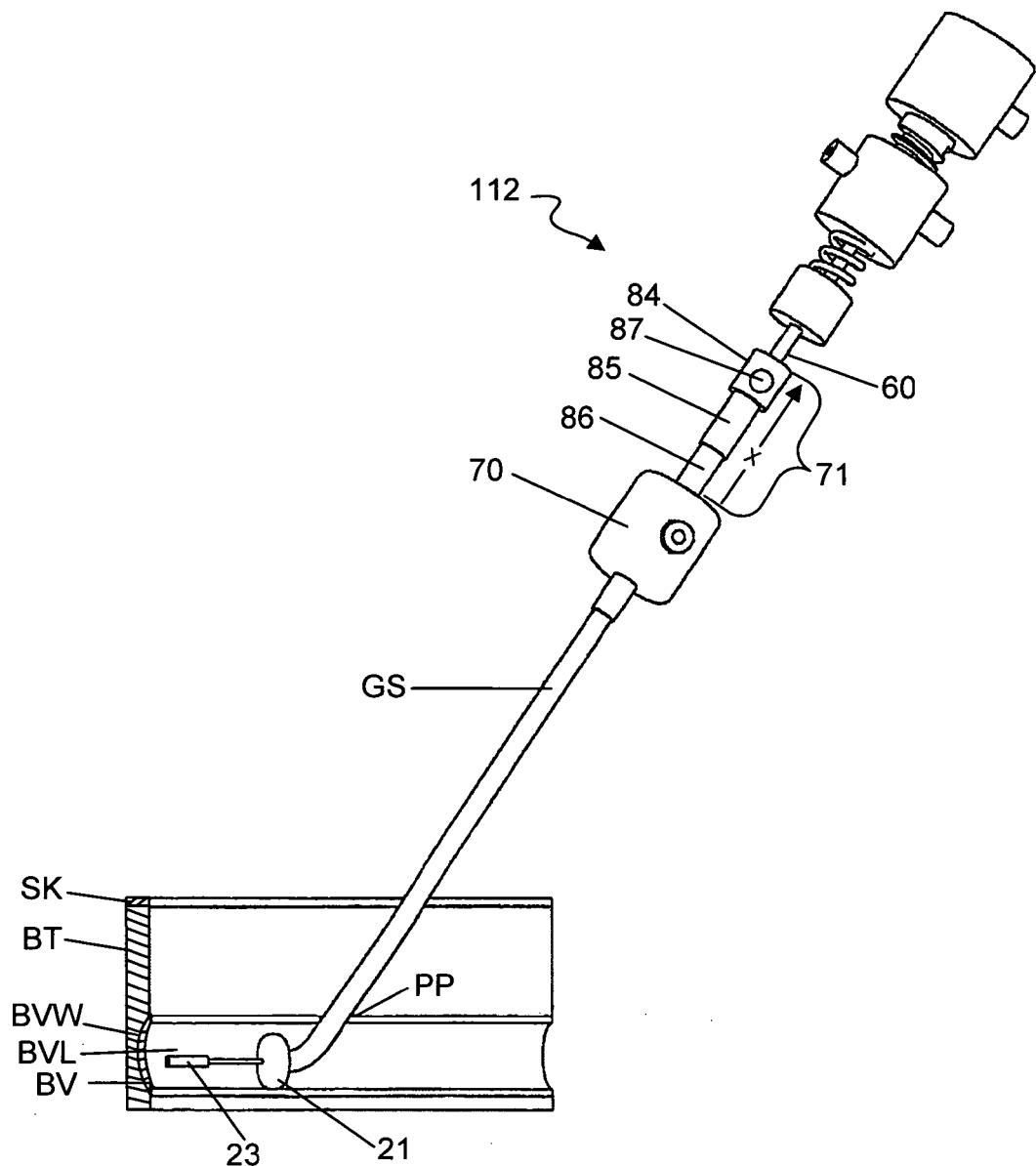
FIG. 9 illustrates an exemplary embodiment with the guide sheath up against tamponading member.
Figure 10:
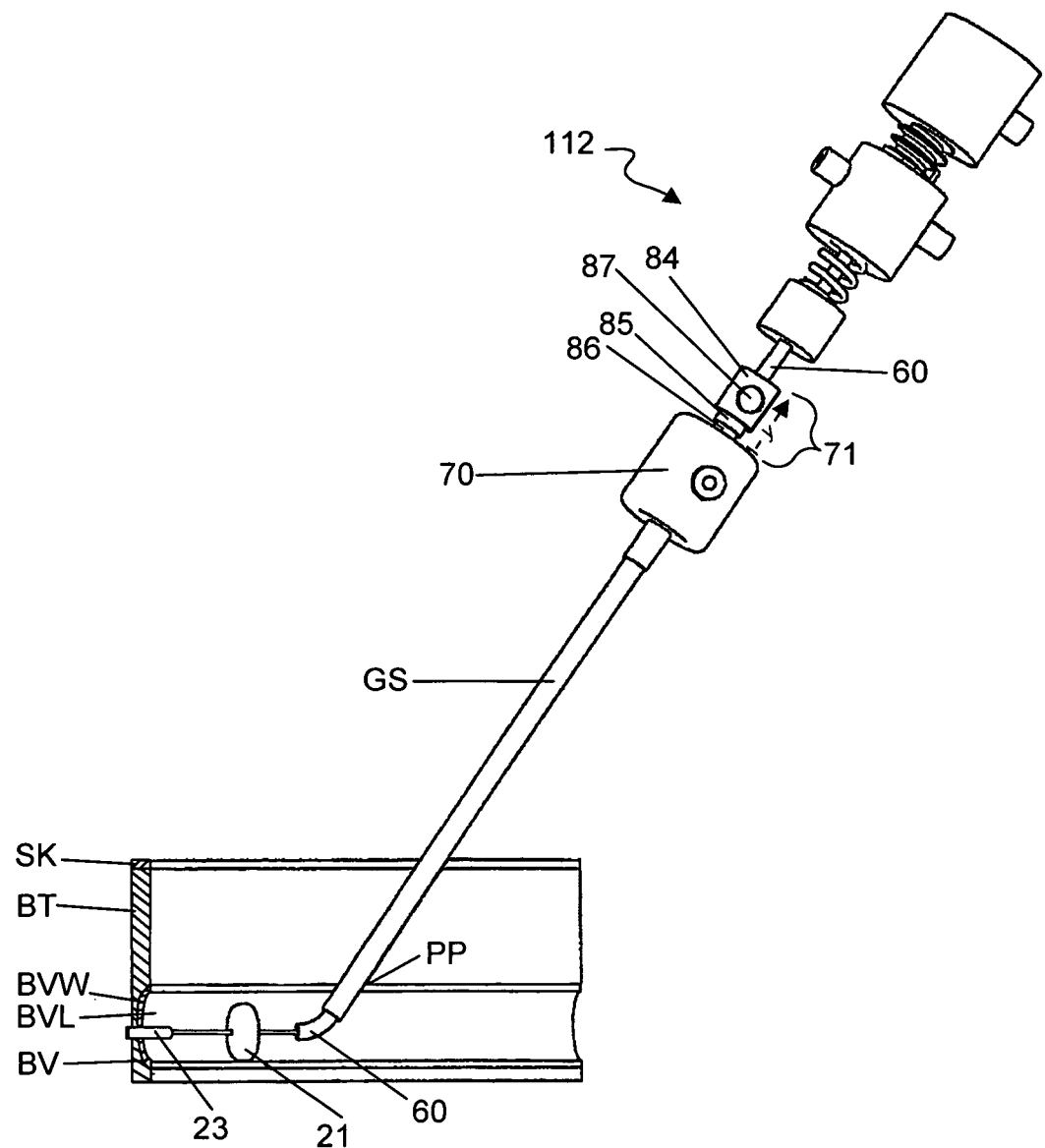
FIG. 10 illustrates an exemplary embodiment with guide sheath retracted back from tamponading member.

FIGS. 9 and 10 show an exemplary embodiment of the sealing system 112 inserted through guide sheath GS. In the exemplary embodiment shown in FIGS. 9 and 10, the guide sheath GS remains in the tract and guide sheaths GS of different lengths may be accommodated.

Guide sheath GS may be in place in puncture PP in connection with a surgical procedure. Guide sheath GS may be manufactured in a variety of different shapes and lengths and the following will illustrate how to accommodate for the variability of guide sheath lengths.

Referring to FIG. 9, sealing system 112 is inserted through the guide sheath GS until tamponading member 21 exits the distal end of guide sheath GS. The tamponading member 21 is activated to an expanded state and sealing system 112 is withdrawn until the distal end of guide sheath GS is in contact with tamponading member 21. Coupling 71 is advanced distally until coupling component 86 is in contact and secured to hub 70 of guide sheath GS. Coupling 71 allows sealing system 112 to be attached to hub 70, and the distal end of guide sheath GS to be within a known distance from tamponading member 21, as will be described. Coupling component 84 is secured to delivery tube 60. Coupling component 84 can be attached to delivery tube 60 through a variety of mechanisms including threads, clips, snaps, protrusions or recesses.

Coupling 71 may include coupling components 84, 85, 86, as shown in FIG. 9. Coupling component 86 may be slidably received in coupling component 85, and coupling component 85 may be slidably received in coupling component 84 to allow for telescoping movement between coupling components 84, 85, 86. The telescoping movement allows the length of coupling 71 (i.e., the distance between the distal end of coupling component 86 or hub 70, and the proximal end of coupling component 84) to be adjustable between length X shown in FIG. 9 to length Y shown in FIG. 10. Accordingly, the length of coupling 71 is adjustable between length X when coupling 71 is in an extended configuration and length Y when coupling 71 is in a collapsed configuration.

Attachment of coupling 71 to guide sheath GS provides a means of setting a defined distance between tamponading member 21, distal end of guide sheath GS and distal end of delivery tube 60. Referring to FIG. 10, once coupling 71 is attached to hub 70, a coupling release mechanism 87 is activated to allow components 85 and 86 to compress (or telescope) together into coupling component 84. Release mechanism 87 can be made by a variety of mechanisms including threads, clips, snaps, protrusions or recesses. For example, release mechanism 87 may include a push button attached to a spring release that permits coupling components 84, 85, 86 to telescope into the collapsed configuration shown in FIG. 10 after pressing the push button.

Since coupling component 84 is secured to delivery tube 60 and coupling component 86 is secured to hub 70 of guide sheath GS, when coupling 71 is collapsed, delivery tube 60 and hub 70 of guide sheath GS are moved with respect to each other. Since tamponading member 21 is connected to delivery tube 60 via connector 14, guide sheath GS also moves with respect to tamponading member 21. The distance that the guide sheath GS moves with respect to tamponading member 21 may generally equal the distance that coupling 71 is shortened (length X-length Y).

Shortening or collapsing coupling 71 retracts guide sheath GS from tamponading member 21 to a set distance (length X-length Y). The set distance between tamponading member 21 and the distal end of guide sheath GS may be 10 mm (0.3937 inch). The set distance can range from 2 mm-20 mm (0.079-0.79 inch). Physicians use a variety of different length guide sheath GS and the method described above provides a means of adjusting and/or consistently setting a distance between the distal end of the guide sheath GS and the tamponading member 21 independent of guide sheath GS length. As a result, coupling 71 allows the physician to move guide sheath GS with respect to tamponading member 21 without pulling guide sheath GS out of puncture PP. Shortening coupling 71 also creates sufficient space between the distal end of guide sheath GS and tamponading member 21 for injecting sealing material.

Figure 11:
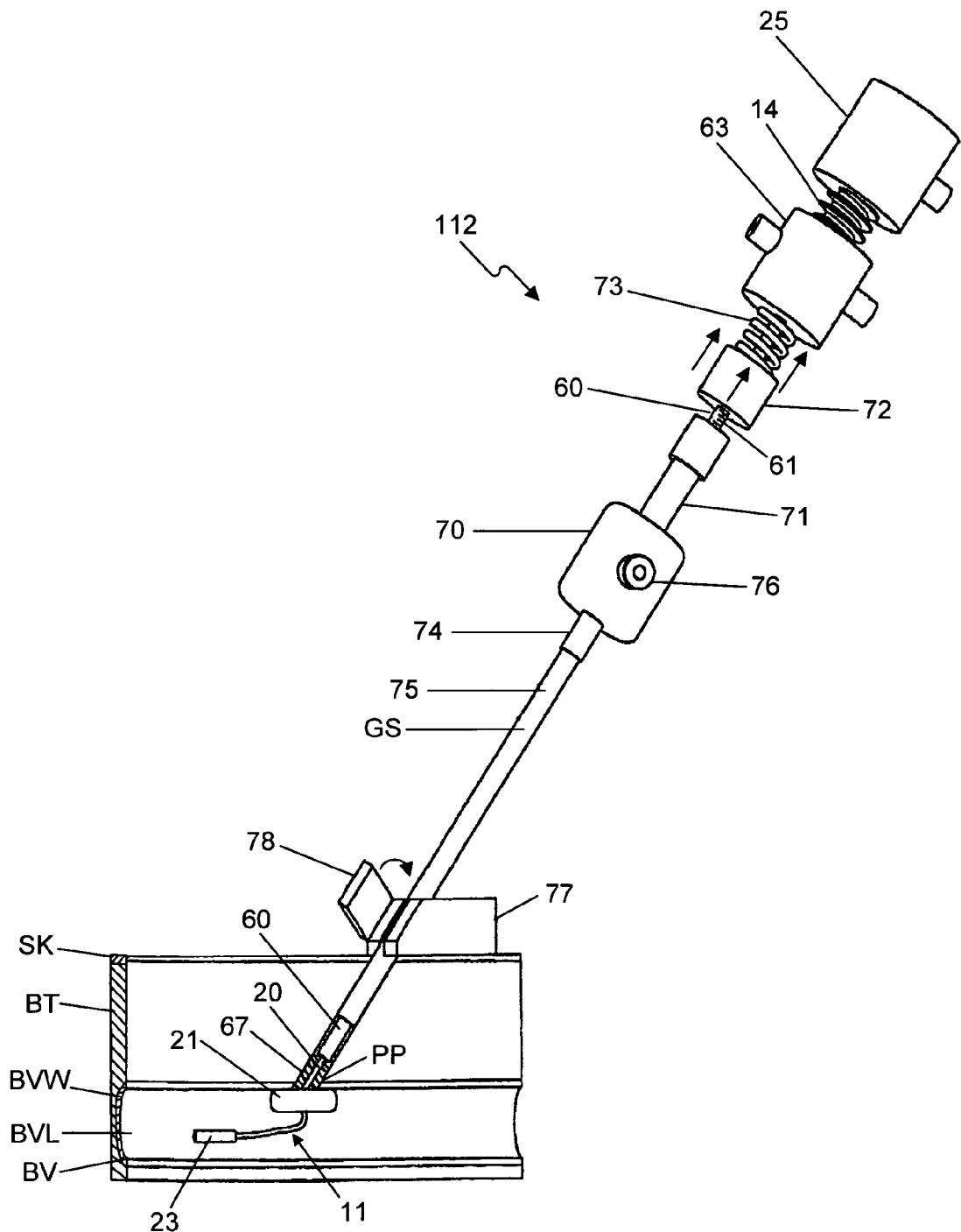
FIG. 11 illustrates an exemplary embodiment with sealing system retracted at a known tension and skin securement hub attached to the guide sheath.

FIG. 11 shows a further embodiment of the sealing system 112 including temporary sealing component 11. In this embodiment, a known tension may be applied to the sealing system 112. As shown in FIG. 11, the sealing system 112 has been retracted so that tamponading member 21 has been pulled up against the puncture PP in the blood vessel wall BVW. To reduce the variability of the amount of tension that is applied to sealing system 112 and the blood vessel wall BVW, a hub 72 and compression spring 73 may be provided.

Delivery tube 60 may be slidably received in hub 72, and hub 72 may be connected to a distal end of compression spring 73. A proximal end of compression spring 73 may be connected to a distal end of first coupling 63. The physician may hold on to and pull hub 72 in the proximal direction (as shown by the arrows in FIG. 11), thereby compressing compression spring 73 and forcing sealing system 112 (e.g., first or second couplings 63, 25) in the proximal direction. As a result, tamponading member 21, which is attached to second coupling 25 by control member 20, is pulled upward against blood vessel wall BVW. The physician may pull hub 72 and sealing system 112 and compress compression spring 73 until a desired force is applied to blood vessel wall BVW.

A scale 61 with numerical indices could be used to help guide the physician to apply a consistent amount of tension. The numerical indices may correspond to the amount of compression of compression spring 73 and may be provided, e.g., on an outer surface of delivery tube 60, as shown in FIG. 11. Applying a known load to sealing system 112 may permit the positioning of tamponading member 21 at a set distance from puncture PP consistently during the delivery of first stage delivery material 67 and bioabsorbable tip 23. Alternatively, or in addition to using compression spring 73, hub 72 may be attached to a variety of other mechanisms including a compression spring, an expansion spring, a polymer band, or other stretchable and/or biasing member.

FIG. 11 shows an embodiment of sealing system 112 in which a skin securement hub 77 may be attached to guide sheath GS. Once a load is applied to sealing system 112 as described above, skin securement hub 77 may be attached to skin SK. Guide sheath GS may be inserted into and positioned within skin securement hub 77, as shown in FIG. 11. Skin securement hub 77 includes a cover 78, which may be closed to secure skin securement hub 77 to guide sheath GS and to secure guide sheath GS and sealing system 112 in position. For example, closing cover 78 onto skin securement hub 77 may cause skin securement hub 77 to be squeezed, compressed, or locked onto guide sheath GS. Skin securement hub 77 can be secured to skin SK using adhesive tape or secured mechanically under skin SK.

Securing the position of sealing system 112 maintains a consistent distance between delivery tube 60 and tamponading member 21 during delivery of the first stage sealing material 67. An additional benefit of securing sealing system 112 in position is that the delivery tube 60 position is maintained during the removal of tamponading member 21 and the separation of bioabsorbable tip 23. Securing sealing system 112 in place also maintains a consistent deployment location of the bioabsorbable tip 23. Also, maintaining position of sealing system 112 with skin securement hub 77 may maintain a consistent delivery location for delivering second stage sealing material 68. Securing sealing system 112 in place with skin securement hub 77 also allows the physician to free one or more hands, which would have been used to hold sealing system 112 in place.

Figure 12:
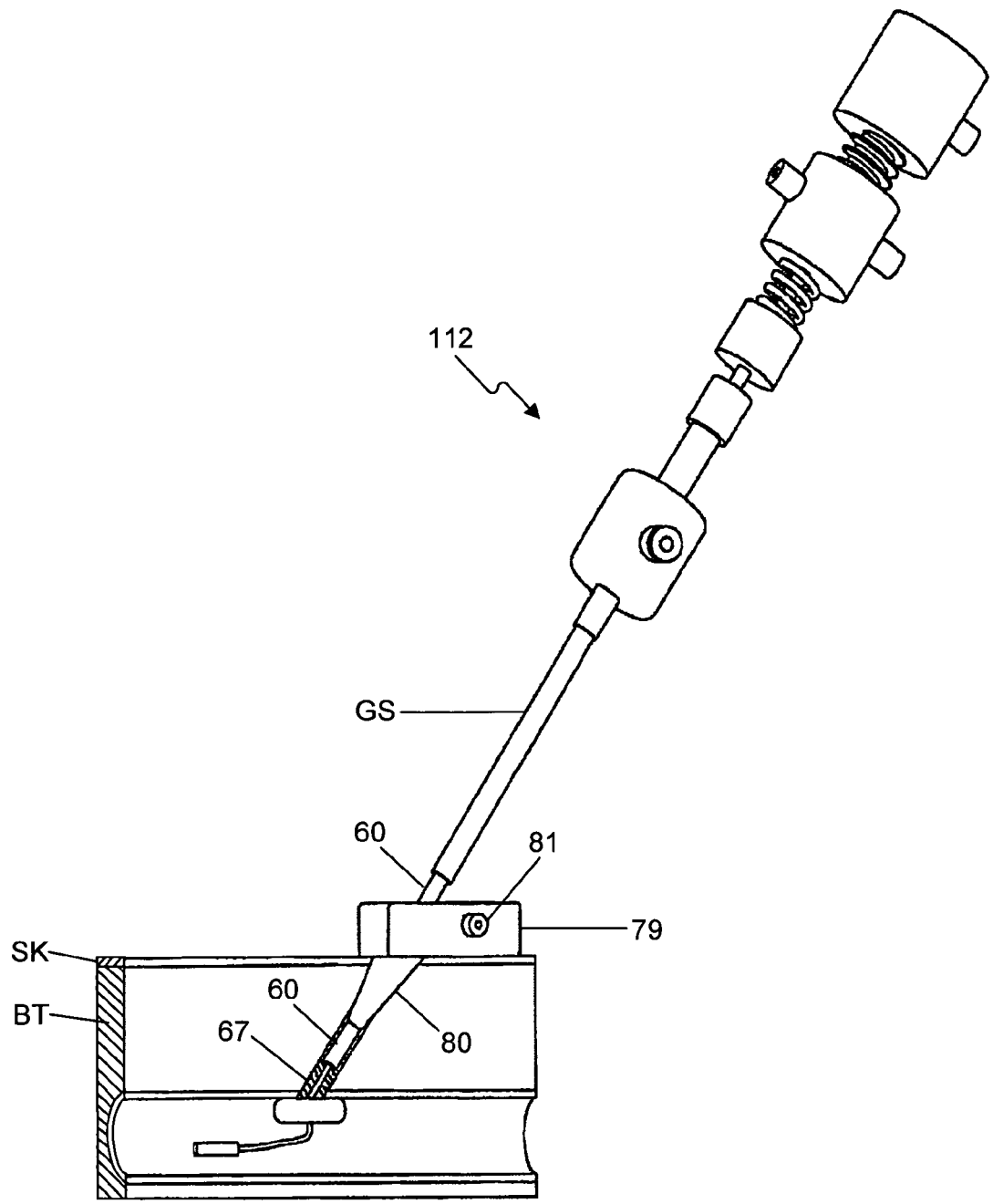
FIG. 12 illustrates an exemplary embodiment with skin securement hub attached to a delivery tube.

FIG. 12 shows an additional embodiment of sealing system 112 secured to a skin securement hub 79 that is attached to delivery tube 60. Skin securement hub 79 may include a cover, e.g., cover 78, and may be secured to delivery tube 60 in a similar manner as described above for securing skin securement hub 77 to guide sheath GS.

Skin securement tube 79 includes a tube 80 inserted through skin SK and body tissue BT. Instead of guide sheath GS, tube 80 may seal the tract, act as a cork, and provide a confined space that forces the first stage sealing material 67 to remain within body tissue BT. A syringe can be attached to luer fitting 81 to apply a vacuum and aspirate fluid from body tissue BT prior to delivery of first stage sealing material 67. Skin securement hub 79 can be secured to skin SK using frictional engagenement or adhesive tape, or is secured mechanically under skin SK.

Figure 13:
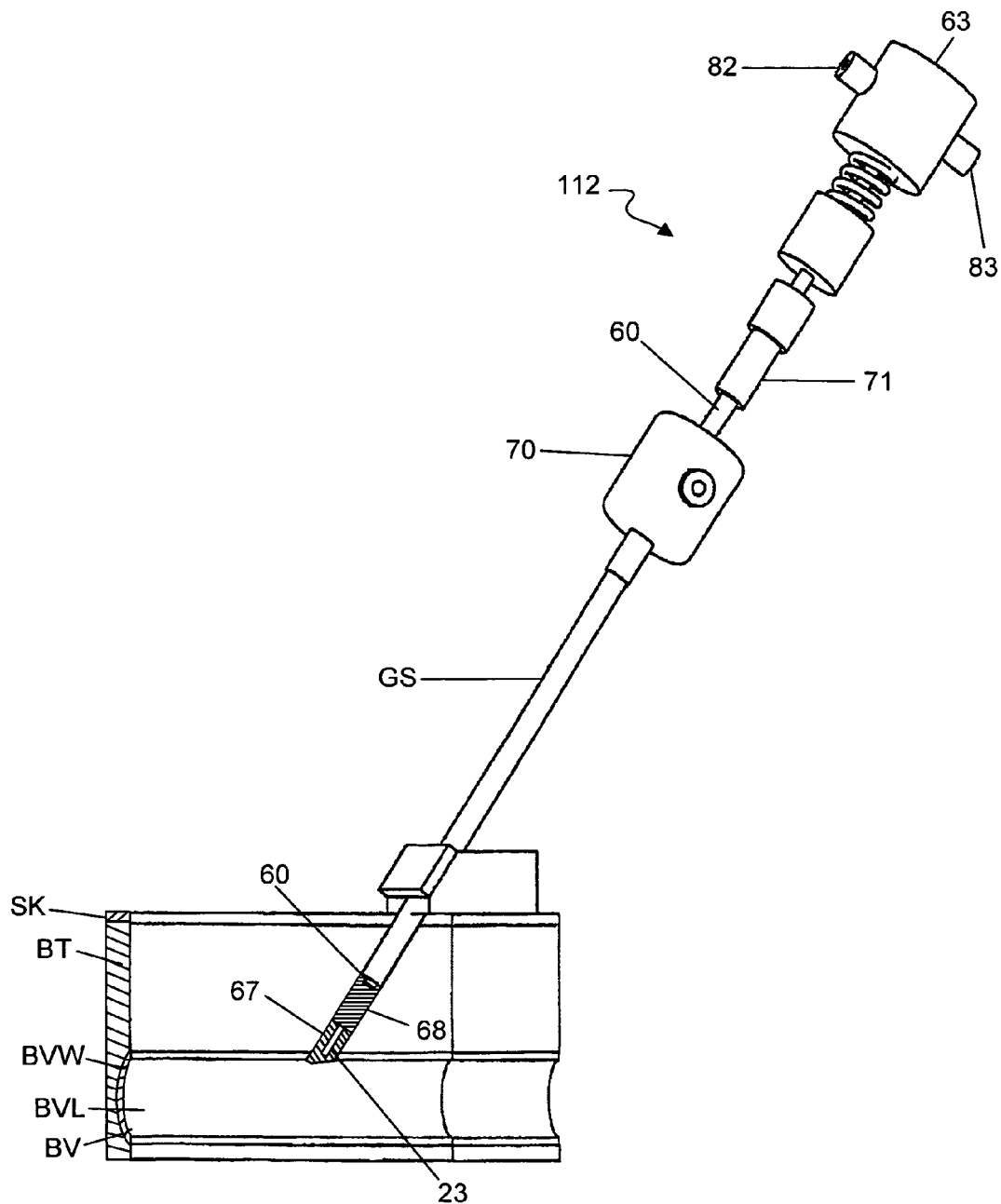
FIG. 13 illustrates an exemplary embodiment with a delivery tube retracted prior to delivery of a second stage of sealing material.

FIG. 13 shows an additional embodiment of sealing system 112 in which delivery tube 60 is retracted prior to delivery of second stage sealing material 68 by retracting coupling 71 from hub 70. A syringe may be attached to a luer fitting 82 in first coupling 63, and luer fitting 82 may be fluidly connected to cavity 31 (FIG. 1) in delivery tube 60 so that first stage sealing material 67 may be delivered from the syringe through cavity 31 in delivery tube 60. After passing through cavity 31, first stage sealing material 67 may seal or block cavity 31. A luer fitting 83 may be provided in first coupling 63 and fluidly connected to cavity 32 (FIG. 1) in delivery tube 60. A syringe may be attached to luer fitting 83 to deliver second stage sealing material 68 through cavity 32 in delivery tube 60.

Prior to delivery of second stage sealing material 68, coupling 71 may be separated from hub 70 to retract coupling 71 from hub 70. While different separation distances may be used, distances on the order of 1-10 mm (0.039-0.39 inch) may be desirable. Alternatively, the retraction of coupling 71 from hub 70 could take place without separating the two components. Coupling 71 and hub 70 could be connected by a hinge mechanism, slide or telescoping tubes (not shown) that allows the physician to retract coupling 71 from hub 70, and retract delivery tube 60 to a predetermined distance. Delivery tube 60 may be retracted so that the distal end of delivery tube 60 is approximately flush with the distal end of guide sheath GS, or so that the delivery tube 60 extends outward from or inward into the distal end of the guide sheath GS up to a distance, e.g., 5 mm, which may be a predetermined distance. Once delivery tube 60 is retracted, second stage sealing material 68 can be delivered through luer fitting 83. The delivery of second stage sealing material 68 seals the remaining channel.

The above disclosure discusses the delivery of second stage sealing material 68, but closure could be completed with only the delivery of first stage sealing material 67 and the delivery of bioabsorbable tip 23.

Figure 14:
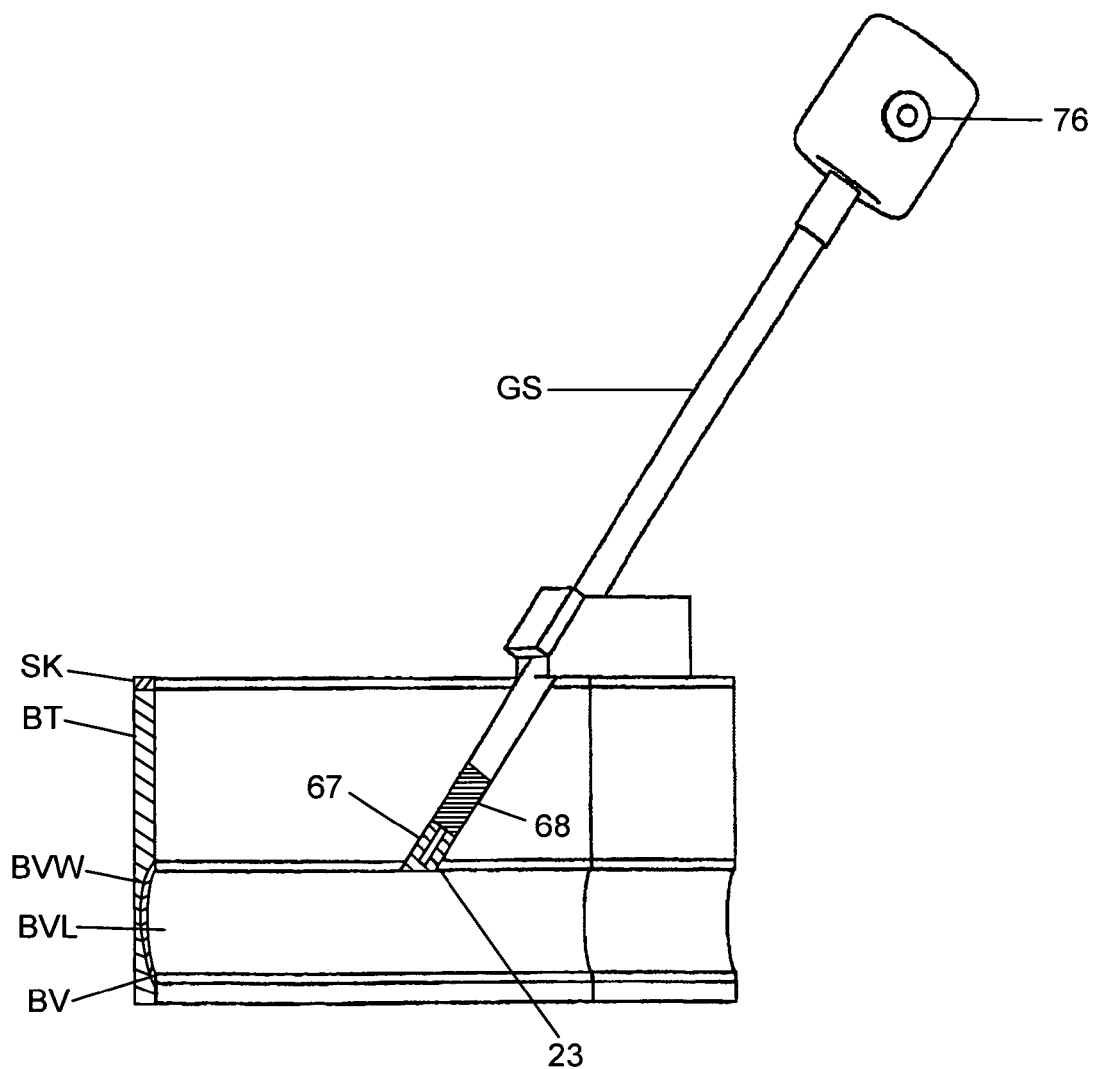
FIG. 14 illustrates an exemplary embodiment delivering the second stage sealing material through the guide sheath.

FIG. 14 shows an additional embodiment that allows the second stage sealing material 68 to be delivered through the guide sheath GS. Prior to delivery of the second stage sealing material 68 the tamponading member 21 and sealing system 112 are removed from the guide sheath GS. Bioabsorbable tip 23 remains in the tract. The second stage sealing material 68 is supplied through luer 76 of the guide sheath GS. The second stage sealing material 68 is injected through the guide sheath GS and seals the remaining channel.

Figure 15:
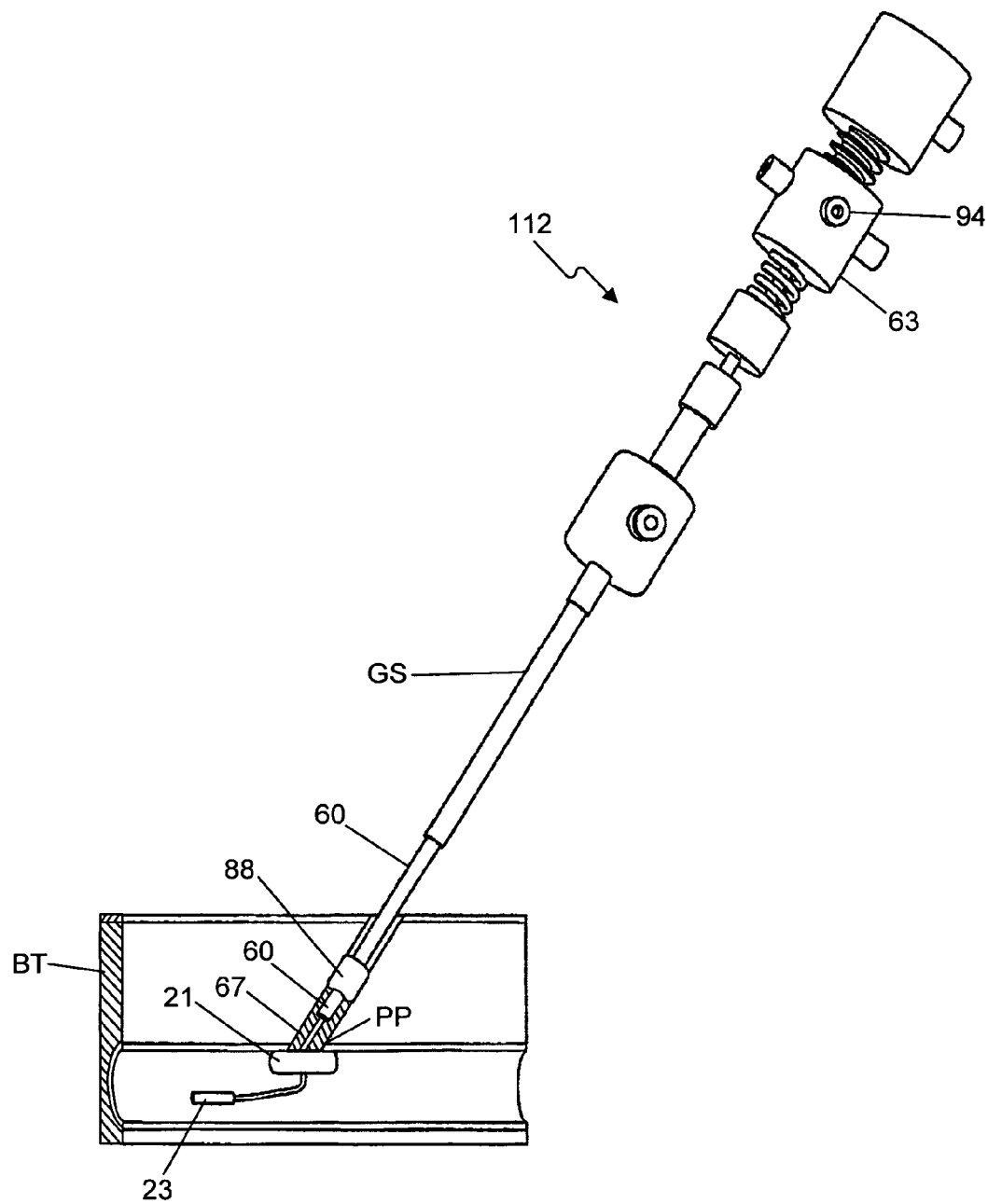
FIG. 15 illustrates an exemplary embodiment with an expandable member attached to a delivery tube and positioned within body tissue.

FIG. 15 shows an additional embodiment of sealing system 112 having an expandable member 88 fixedly attached to delivery tube 60 and expanded within body tissue BT. Sealing system 112 is inserted through guide sheath GS. Tamponading member 21 is expanded and sealing system 112 is retracted so that tamponading member 21 is pulled up against the puncture PP in the blood vessel wall BVW. Guide sheath GS is retracted from body tissue BT.

Delivery tube 60 may include an additional channel (not shown) fluidly connecting expandable member 88 to a luer 89 in first coupling 63. A syringe may be attached to luer 89 to deliver gas or liquid through the channel in delivery tube 60 to expand or contract the expandable member 88.

Expandable member 88 provides numerous benefits. For example, the position of sealing system 112 may be secured to maintain a consistent distance between delivery tube 60 and tamponading member 21 during delivery of the first stage sealing material 67. An additional benefit of securing sealing system 112 in position is that the delivery tube 60 position is maintained during the removal of tamponading member 21 and the separation of bioabsorbable tip 23. Securing sealing system 112 in place maintains a consistent deployment location of the bioabsorbable tip 23. Also, maintaining position of sealing system 112 may maintain a consistent delivery location for delivering second stage sealing material 68. An additional benefit of expanding expandable member 88 is that the expandable member 88 seals the tract and/or acts as a cork and provides a confined space that forces the sealing material to remain within the body tissue BT. The expandable member 88 can be created by many means, such as, expandable balloon, expandable disc, telescoping tubes, etc.

Figure 16:
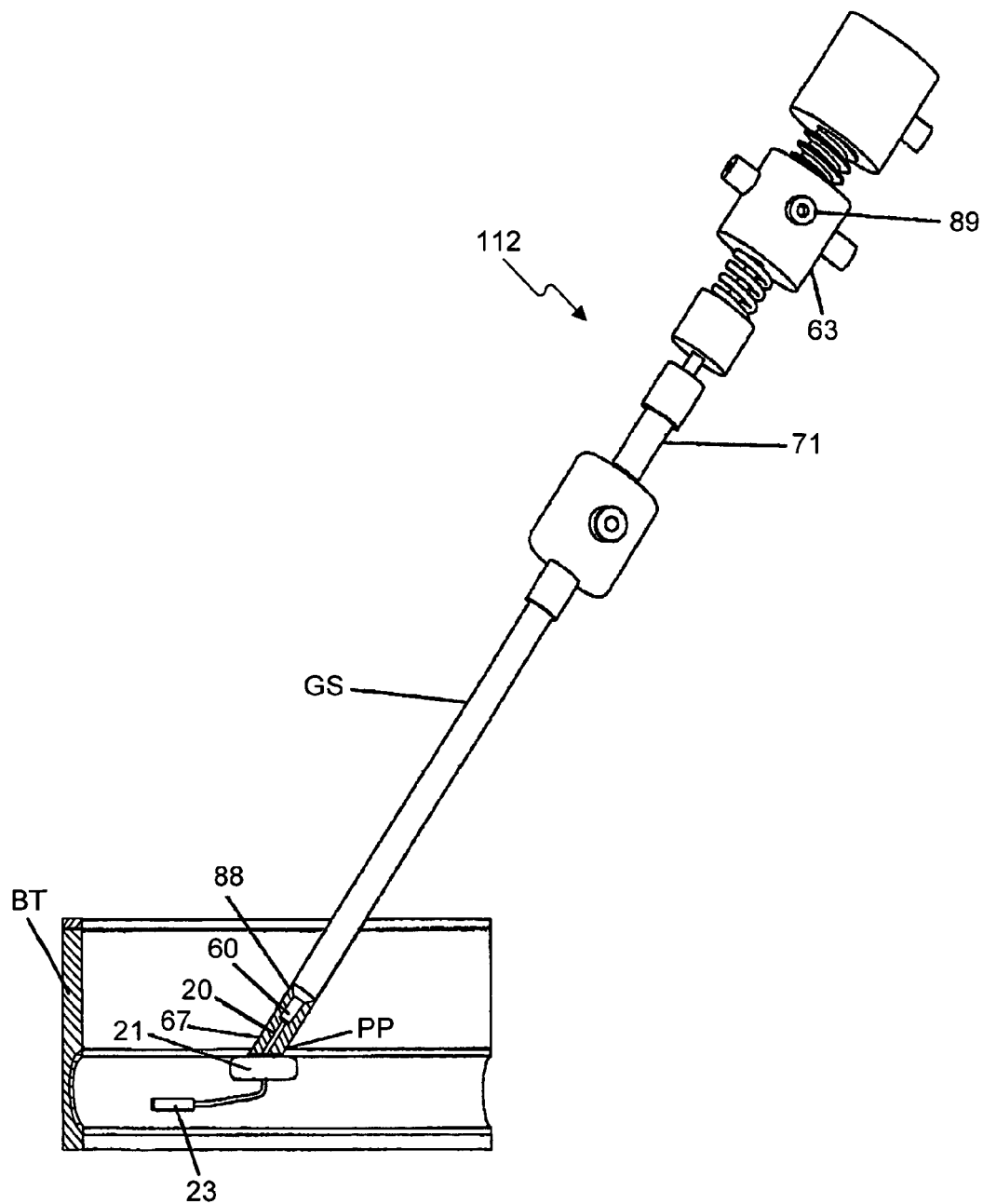
FIG. 16 illustrates an exemplary embodiment with an expandable member attached to a delivery tube and positioned within the guide sheath.

FIG. 16 shows an additional embodiment of sealing system 112 with expandable member 88 fixedly attached to delivery tube 60 and expanded within guide sheath GS. Sealing system 112 is inserted through guide sheath GS. Tamponading member 21 is expanded and sealing system 112 is retracted so that tamponading member 21 is pulled up against the puncture PP in the blood vessel wall BVW. Guide sheath GS is retracted and secured onto coupling 71. A syringe may be attached to luer 89 as described above to deliver gas or liquid through the channel in delivery tube 60 to expand or contract the expandable member 88.

Expandable member 88 provides numerous benefits. For example, the expandable member 88 seals the guide sheath GS and/or acts as a cork and prevents the first stage delivery material 67 from entering the guide sheath GS. An additional benefit is the ability to center the sealing system 112 and control member 20 within the percutaneous puncture PP. Centering control member 20 may help facilitate centering the hollow space or tract within first stage sealing material 67 and positioning bioabsorbable tip 23 within the center of the percutaneous puncture PP. This is beneficial when closing larger bore percutaneous punctures PP, such as punctures PP produced by a 12-24 french guide sheath. The position of the expandable member could be completely within the guide sheath GS or partially exiting the distal end of guide sheath GS.

According to another exemplary embodiment, the tamponading member 21 may serve as a bioabsorbable tip, and a separate bioabsorbable tip (e.g., bioabsorbable tip 23) may be omitted. Referring to the hollow passage or tract in the first stage sealing material 67, as the tamponading member 21 is collapsed and retracted, the tamponading member 21 passes into the tract in the first stage sealing material 67 and serves to fill the hollow space defined by the tract. In this way, the tamponading member 21 may become the bioabsorbable tip 23 and may provide an improved method for completely sealing the puncture PP. Tamponading member 21 and/or bioabsorbable tip 23 can be made from a variety of materials including polyethylene glycol, polylactic acid, polyglycolic acid, collagen, poly-ether-ester or a combination of these or other bioabsorbable materials. Alternatively, tamponading member 21 and/or tip 23 may be nonbioabsorbable. Other materials for forming tamponading member 21 and/or tip 23 may include stainless steel, titanium, nitinol, P.E.E.K., P.E.T., silk, hydrogel, a two-part liquid compound, etc. A variety of mechanisms may be employed to release tamponading member 21 from the catheter so that it may be deposited in the tract in the first stage sealing material 67. For example, tamponading member 21 may be released using a mechanical or electro-mechanical release mechanism, including any of the mechanisms described in this disclosure, or by fracturing or breaking off a portion of tamponading member 21.

Figure 17:
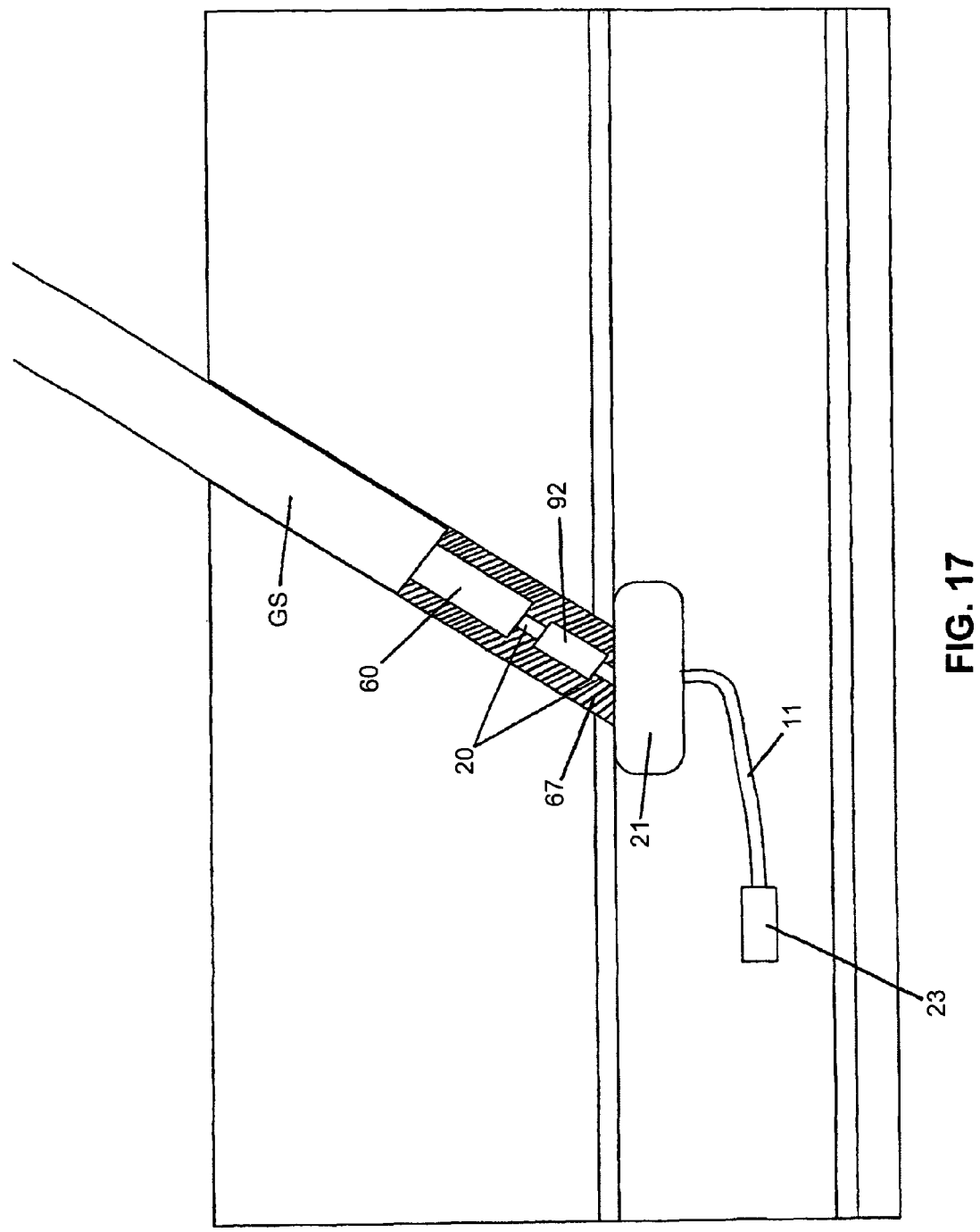
FIG. 17 illustrates an exemplary embodiment of a sealing system delivering first stage sealing material to create a hollow cavity for positioning a tip.
Figure 18:
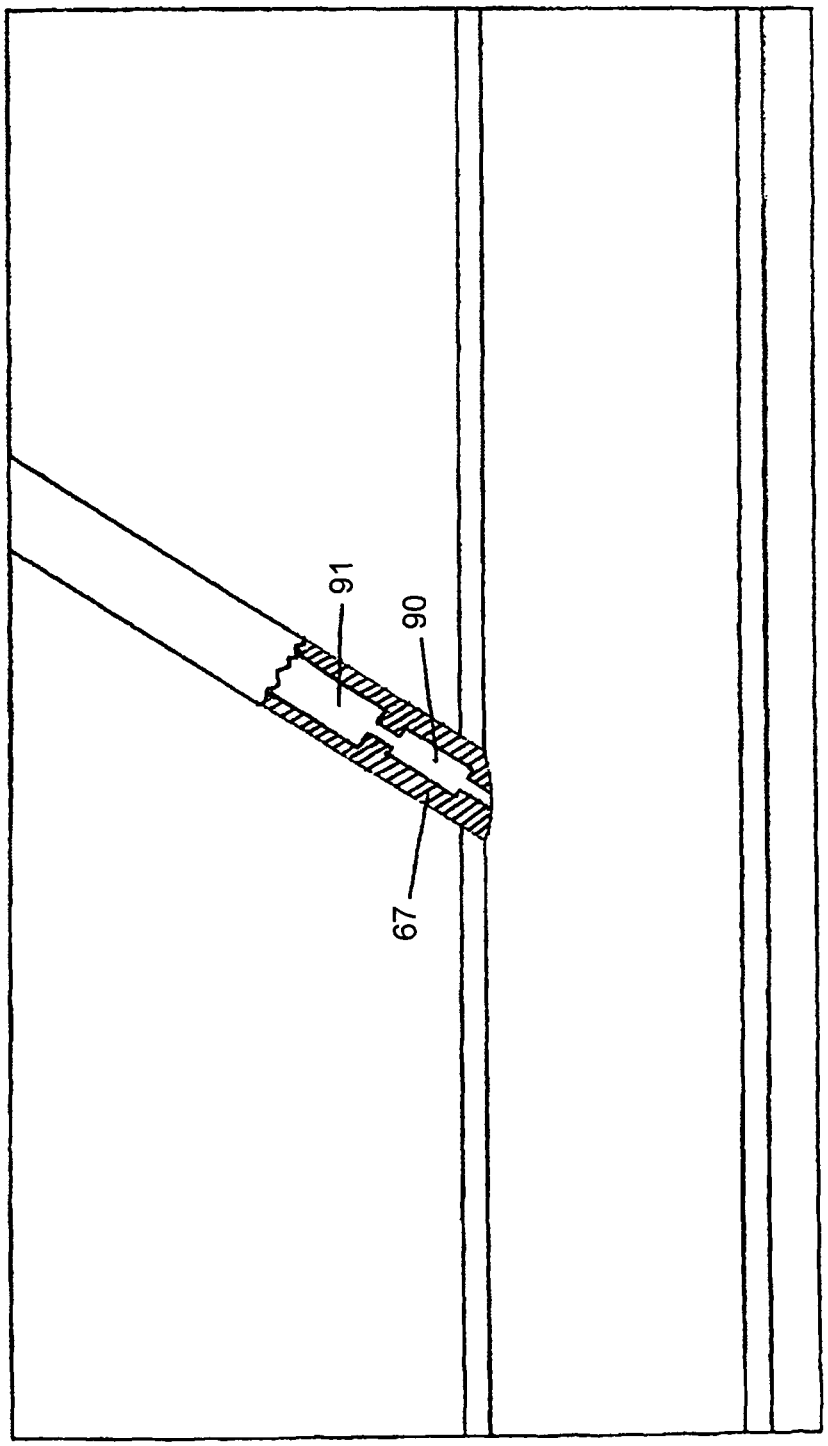
FIG. 18 illustrates an exemplary embodiment of a hollow cavity created by a sealing system after first stage sealing material is delivered.
Figure 19:
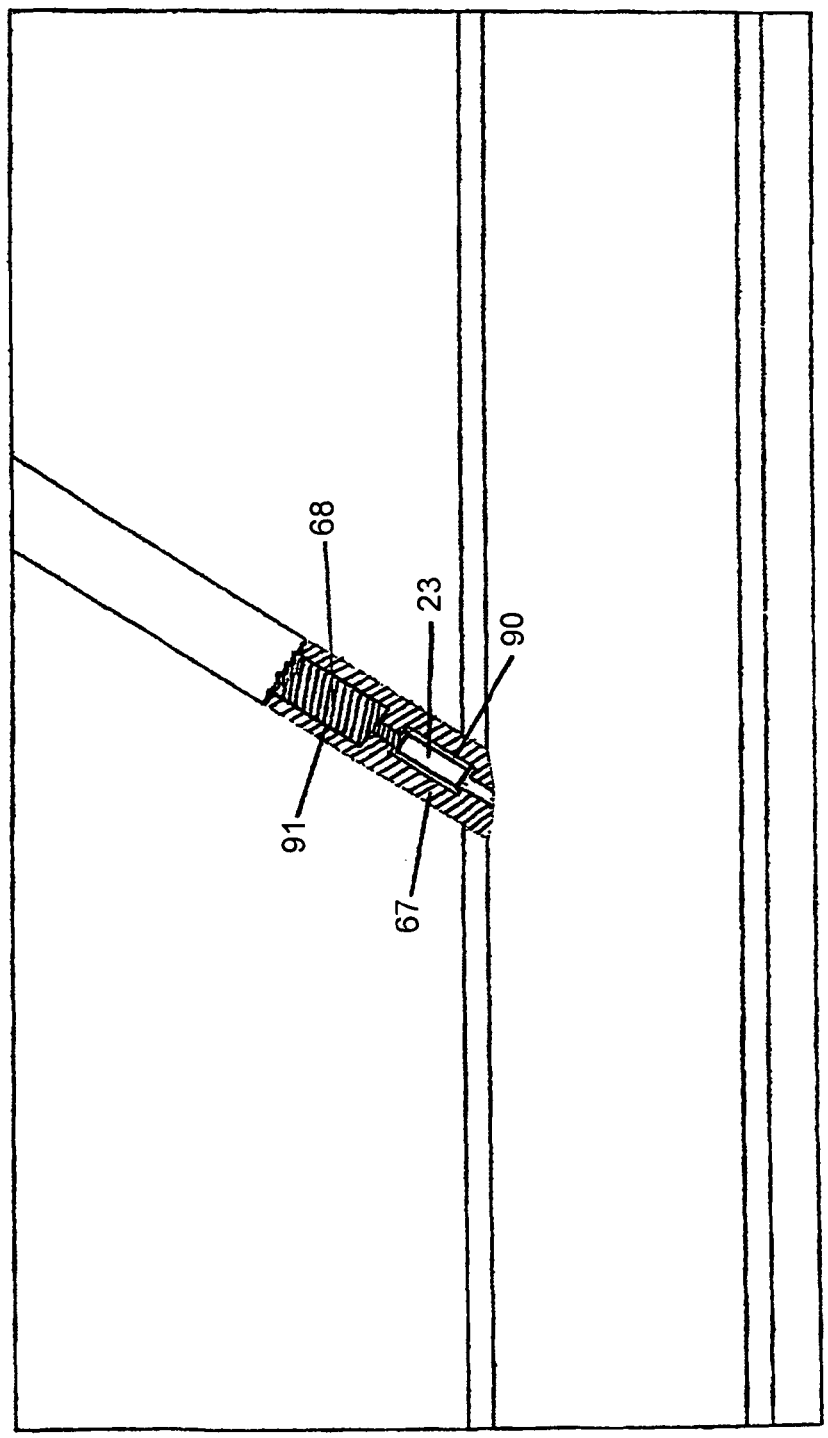
FIG. 19 illustrates an exemplary embodiment of a tip and second stage sealing material positioned within a hollow cavity.

FIGS. 17-19 show an exemplary embodiment of sealing system 112 with an insert member 92 attached to control member 20. Insert member 92 creates a hollow cavity 90, which may be a hollow geometry pocket with a defined shape within first stage sealing material 67. The size and/or shape of hollow cavity 90 may be similar to the size and/or shape of bioabsorbable tip 23. During the withdrawal of temporary sealing component 11 from first stage sealing material 67, bioabsorbable tip 23 may be disconnected from temporary sealing component 11 and positioned within hollow cavity 90.

As shown in FIG. 17, insert member 92 on control member 20 may be positioned in percutaneous puncture PP during the delivery of first stage sealing material 67.

As shown in FIG. 18, after first stage sealing material 67 is delivered and set, one or more hollow cavities 90, 91 may be formed in first stage sealing material 67. For example, hollow cavity 90 may be created by removing insert member 92 from first stage sealing material 67 after first stage sealing material 67 has set, and/or hollow cavity 91 may be created by removing delivery tube 60 from first stage sealing material 67 after first stage sealing material 67 has set.

As shown in FIG. 19, when insert member 92 on control member 20 of temporary sealing component 11 is retracted, bioabsorbable tip 23 may be positioned within hollow cavity 90 and released as described above in connection with FIGS. 6 and 7, or in any other suitable fashion. Second stage sealing material 68 may be delivered within hollow cavity 91.

Hollow cavity 90 may have one of many different shapes depending on the geometry of insert member 92. Insert member 92 may be smaller or approximately the same size as bioabsorbable tip 23. Hollow cavity 90 may be smaller than bioabsorbable tip 23 to help secure bioabsorbable tip 23 and prevent second stage sealing material 68 from traveling distally during injection of second stage sealing material 68.

Insert member 92 may have a fixed shape or may be expandable to create a larger shape prior to the delivery of first stage delivery material 67. For example, expandable insert member 92 may be a balloon. Expandable insert member 92 may be positioned in percutaneous puncture PP in a nonexpanded condition and expanded prior to delivering first stage sealing material 67 to the percutaneous puncture PP (FIG. 17). After delivering first stage sealing material 67, the expanded insert member 92 may be changed to its nonexpanded shape and removed from hollow cavity 90 (FIG. 18). Then, bioabsorbable tip 23 may be positioned within hollow cavity 90 (FIG. 19).

Alternatively, insert member 92 may be formed from a flexible (e.g., a gummy, elastic, etc.) material that allows insert member 92 to change shape and/or be squeezed to allow insert member 92 to be inserted into and removed from hollow cavity 90. The expandable insert member 92 may be positioned in percutaneous puncture PP in an unstressed (or normal) shape and/or condition prior to delivering first stage sealing material 67 to the percutaneous puncture PP (FIG. 17). After delivering first stage sealing material 67, control member 20 may be pulled proximally with respect to the puncture so that insert member 92 is pulled out of hollow cavity 90 (FIG. 18). As insert member 92 is pulled, insert member 92 may change shape and/or be squeezed through a narrower cavity formed by control member 20 in first stage sealing material 67 proximal to hollow cavity 90 (e.g., a narrow cavity formed between hollow cavity 90 and hollow cavity 91). Then, bioabsorbable tip 23 may be positioned within hollow cavity 90 (FIG. 19).

The shape of insert member 92 may be one of the various shapes described in this disclosure for bioabsorbable tip 23. Insert member 92 may be formed of one or more of the materials described above for forming bioabsorbable tip 23. Insert member 92 may be formed integrally with control member 20, or may be formed separate from control member 20 and attached to control member 20.

A variety of methods may be used to determine and monitor the location of bioabsorbable tip 23 prior to its separation from temporary sealing component 11. As described above, pulling tamponading member 21 against the interior of blood vessel wall BVW allows the surgeon to confirm the location of sealing system 10, 112 and delivery tube 60. Also, a clip may be installed on delivery tube 60 to indicate where delivery tube 60 exits skin SK and to assist in determining the distance between distal end 64 of delivery tube 60 and blood vessel wall BVW. Then, the location of bioabsorbable tip 23 may be determined based on the location of distal end 64 of delivery tube 60 since the distance between temporary sealing component 11 and sealing material delivery component 12 (e.g., adjusted using connector 14) is known.

Blood pressure may also be used to assist the user to identify the position of bioabsorbable tip 23 prior to its detachment from temporary sealing component 11. A pressure transducer (not shown) may be attached to temporary sealing component 11 and may provide an arterial pressure reading that may be recorded while temporary sealing component 11 is within blood vessel lumen BVL. While temporary sealing component 11 is withdrawn from blood vessel lumen BVL, the arterial pressure may be monitored until a pressure drop occurs (e.g., when pressure drops a predetermined amount), which may indicate that bioabsorbable tip 23 is positioned within first stage sealing material 67.

Another method of identifying the location of bioabsorbable tip 23 is with the use of blood flow. Temporary sealing component 11 may include a lumen (not shown), e.g., located in wire 27 with a distal opening that is distal or proximal to bioabsorbable tip 23. The user may allow a small amount of blood to flow through the lumen while bioabsorbable tip 23 is within blood vessel lumen BVL. Stoppage of the blood flow in the lumen may indicate that bioabsorbable tip 23 is withdrawn and positioned within first stage sealing material 67.

Another method of identifying the location of bioabsorbable tip 23 is with the use of fluoroscopy or other imaging techniques used to view internal structures of a patient. A radiopaque filler or marker or other type of identifiable material may be placed within bioabsorbable tip 23. The user may watch, e.g., on a fluoroscope, the movement of the radiopaque marker to identify when bioabsorbable tip 23 is positioned within first stage sealing material 67. Radiopaque fillers or markers may also be added to first stage sealing material 67 to help visualize first stage sealing material 67 during delivery.

Bioabsorbable tip 23 may be formed in one of a variety of shapes. For example, as shown in FIGS. 2-17, bioabsorbable tip 23 may be elongate with a cylindrical, rectangular, or other type of cross section. FIGS. 20-27 show exemplary embodiments of the various shapes that bioabsorbable tip 23 may have.

Figure 20:
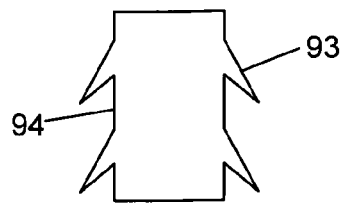
FIG. 20 illustrates an exemplary embodiment of a tip with barbs secured to the sides of a body.

FIG. 20 shows an embodiment of bioabsorbable tip 23 with a body 94, and one or more barbs 93 secured to the sides of body 94. Barbs 93 may be flexible and may allow bioabsorbable tip 23 to pass through first stage sealing material 67 in one direction, e.g., proximally, with a small amount of resistance. Barbs 93 may open or catch, and become engaged or lock on to first stage sealing material 67 to prevent bioabsorbable tip 23 from moving distally. Barbs 93 may be made of rigid, semi-rigid, or soft materials. As shown in FIG. 20, barbs 93 may be pointed or tapered, and may extend from body 94 at an angle relative to a longitudinal axis of body 94. Barbs 93 may be angled towards a distal end of body 94. Barbs 93 may provide a liquid seal between bioabsorbable tip 23 and first stage sealing material 67. As a result, when delivering second stage sealing material 68, barbs 93 may prevent second stage sealing material 68 from entering blood vessel lumen BVL. Barbs 93 may also prevent blood from flowing proximally past bioabsorbable tip 23.

Figure 21:
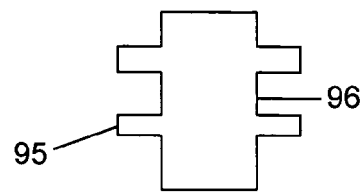
FIG. 21 illustrates an exemplary embodiment of a tip with rings around a body.

FIG. 21 shows an embodiment of bioabsorbable tip 23 with a body 96, and one or more rings 95 around body 96. Rings 95 may be constructed of the same material as body 96 and may be formed integral with body 96. Rings 95 may be flexible or rigid. Rings 95 may provide stability to bioabsorbable tip 23 within first stage sealing material 67. Rings 95 may also provide a liquid seal between bioabsorbable tip 23 and first stage sealing material 67. As a result, when delivering second stage sealing material 68, rings 95 may prevent second stage sealing material 68 from entering blood vessel lumen BVL. Rings 95 may also prevent blood from flowing proximally past bioabsorbable tip 23.

Figure 22:
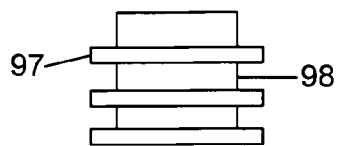
FIG. 22 illustrates an exemplary embodiment of a tip with independent rings around a body.

FIG. 22 shows an embodiment of bioabsorbable tip 23 with a body 98, and one or more rings 97 around body 98. Rings 97 may be made of a different material than body 98. Rings 97 may be flexible or rigid. Rings 97 may provide stability to bioabsorbable tip 23 within first stage sealing material 67. Rings 97 may also provide a liquid seal between bioabsorbable tip 23 and first stage sealing material 67. As a result, when delivering second stage sealing material 68, rings 97 may prevent second stage sealing material 68 from entering blood vessel lumen BVL. Rings 97 may also prevent blood from flowing proximally past bioabsorbable tip 23.

Figure 23:
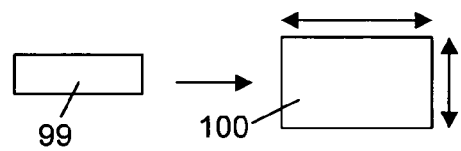
FIG. 23 illustrates an exemplary embodiment of a tip that is expandable.

FIG. 23 shows an embodiment of bioabsorbable tip 23 that is expandable. For example, bioabsorbable tip 23 may be formed from expandable materials, such as materials that expand when in contact with a liquid, e.g., blood. Alternatively, bioabsorbable tip 23 may include an expandable structure, e.g., an expandable balloon, and the size of the expandable structure may be controlled by the user. Bioabsorbable tip 23 may enter blood vessel lumen BVL in the smaller, unexpanded configuration 99, and may be opened or expanded to the larger, expanded configuration 100 when in contact with blood or otherwise activated. The expanded configuration 100 may provide stability to bioabsorbable tip 23 within first stage sealing material 67. When expanded, a liquid seal may form between bioabsorbable tip 23 and first stage sealing material 67. As a result, when delivering second stage sealing material 68, expanded configuration 100 of bioabsorbable tip 23 may prevent second stage sealing material 68 from entering blood vessel lumen BVL. Expanded configuration 100 of bioabsorbable tip 23 may also prevent blood from flowing proximally past bioabsorbable tip 23.

Figure 24:
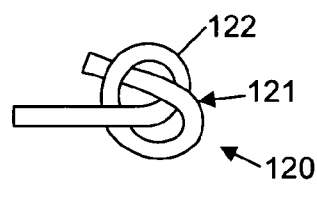
FIG. 24 illustrates an exemplary embodiment of a tip constructed of a suture with a knot tied within a main body of the suture.

FIG. 24 shows an embodiment of bioabsorbable tip 23 including a suture 120. Suture 120 may include a main body 121 with a knot 122 tied within main body 122 of suture 120.

Figure 25:
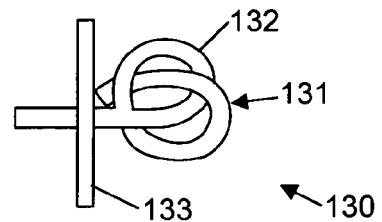
FIG. 25 illustrates an exemplary embodiment of a tip constructed of a suture with a knot tied within the main body with a disc.

FIG. 25 shows an embodiment of bioabsorbable tip 23 including a suture 130. Suture 130 may include a main body 131 with a knot 132 tied within main body 131 of suture 130. A flexible or rigid disc 133 may be located on suture 130 proximal to the knot 132.

Each suture 120, 130 shown in FIGS. 24 and 25 may provide stability to bioabsorbable tip 23 within first stage sealing material 67. Each suture 120, 130 may also provide a liquid seal between bioabsorbable tip 23 and first stage sealing material 67. As a result, when delivering second stage sealing material 68, each suture 120, 130 may prevent second stage sealing material 68 from entering blood vessel lumen BVL. Each suture 120, 130 may also prevent blood from flowing proximally past bioabsorbable tip 23.

Figure 26:
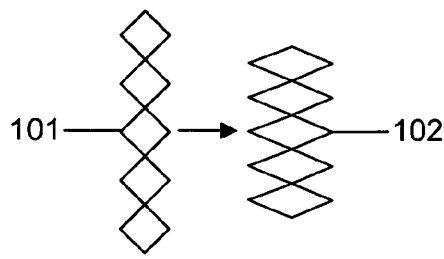
FIG. 26 illustrates an exemplary embodiment of a tip constructed of a braid configuration.

FIG. 26 shows an embodiment of bioabsorbable tip 23 including a braid configuration. The braid may be stretched to a lower picks per inch configuration 101 and compressed to a higher picks per inch 102 configuration. The higher picks per inch configuration 102 increases an outer dimension of the braid (e.g., the thickness, width, diameter, etc., of the braid) to assist in securing bioabsorbable tip 23 within first stage sealing material 67. The lower picks per inch configuration 101 provides a smaller outer dimension that may facilitate delivery of bioabsorbable tip 23 within first stage sealing material 67. The braid may include a plurality of strands that are braided together so that, when second stage delivery material 68 is delivered, second stage sealing material 68 may mold around the individual strands of the braid to help secure bioabsorbable tip 23 in place. In higher picks per inch configuration 102, the braid may provide stability to bioabsorbable tip 23 within first stage sealing material 67, and a liquid seal may form between bioabsorbable tip 23 and first stage sealing material 67. As a result, when delivering second stage sealing material 68, higher picks per inch configuration 102 of bioabsorbable tip 23 may prevent second stage sealing material 68 from entering blood vessel lumen BVL. Higher picks per inch configuration 102 of bioabsorbable tip 23 may also prevent blood from flowing proximally past bioabsorbable tip 23. Alternatively, bioabsorbable tip 23 may include other configurations that are capable of stretching to decrease an outer dimension of bioabsorbable tip 23 and compressing to increase an outer dimension of bioabsorbable tip 23, such as a bellows-like configuration.

Figure 27:
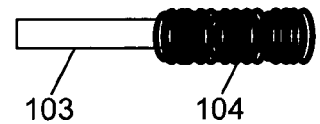
FIG. 27 illustrates an exemplary embodiment of a tip constructed of a semi-rigid body with a soft pliable end.

FIG. 27 shows an embodiment of bioabsorbable tip 23 constructed of a body 103 with a soft pliable end 104. Body 103 may be semi-rigid so that bioabsorbable tip 23 is similar to a cotton swab. Pliable end 104 may be formed of a material that is fibrous, porous, spongy, etc. Pliable end 104 may provide stability to bioabsorbable tip 23 within first stage sealing material 67 and may also provide a liquid seal between bioabsorbable tip 23 and first stage sealing material 67. As a result, when delivering second stage sealing material 68, pliable end 104 may prevent second stage sealing material 68 from entering blood vessel lumen BVL. Pliable end 104 may also prevent blood from flowing proximally past bioabsorbable tip 23.

The sizes of the various embodiments of bioabsorbable tip 23 described above may vary. For example, bioabsorbable tip 23 may be smaller, larger, or generally the same size as the hollow cavity 90 or other tract formed within first stage sealing material 67.

Bioabsorbable tip 23 may be positioned in one of a variety of locations with respect to first and second stage sealing materials 67, 68. FIGS. 28-31 show exemplary embodiments of locations of bioabsorbable tip 23 with respect to first and second stage sealing materials 67, 68.

Figure 28:
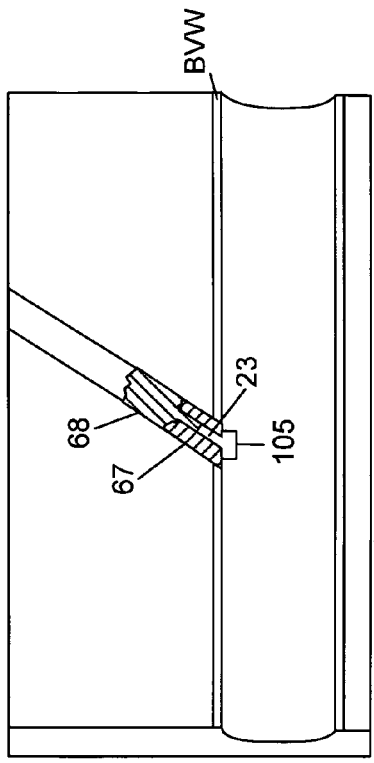
FIG. 28 illustrates an exemplary embodiment of a tip positioned within first stage sealing material and second stage sealing material.

FIG. 28 shows an embodiment of bioabsorbable tip 23 positioned within both first stage sealing material 67 and second stage sealing material 68. Bioabsorbable tip 23 may include a distal flange 105 and a proximal flange 106. Distal flange 105 may extend through blood vessel wall BVW and may prevent bioabsorbable tip 23 from moving proximally. Proximal flange 106 may rest within first stage sealing material 67, within second stage sealing material 68, or within both first and second stage sealing materials 67, 68. Proximal flange 106 may prevent bioabsorbable tip 23 from moving distally or proximally. Both distal and proximal flanges 105, 106 may also provide a seal between bioabsorbable tip 23 and first and second stage sealing materials 67, 68, e.g., to prevent second stage sealing material 68 from entering blood vessel lumen BVL.

Figure 29:
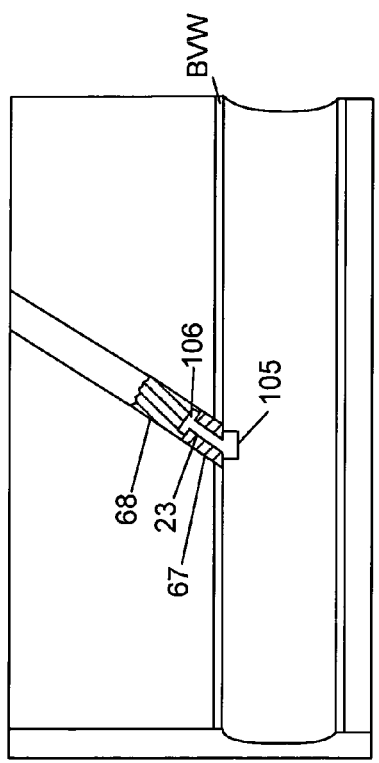
FIG. 29 illustrates an exemplary embodiment of a tip positioned within first stage sealing material.

FIG. 29 shows an embodiment of bioabsorbable tip 23 positioned within first stage sealing material 67. In this embodiment, bioabsorbable tip 23 may include distal flange 105, which may extend through blood vessel wall BVW and may prevent bioabsorbable tip 23 from moving proximally.

Figure 30:
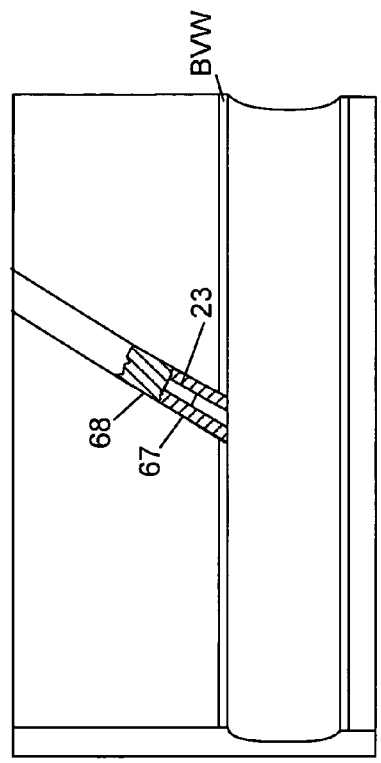
FIG. 30 illustrates an exemplary embodiment of a tip positioned in close proximity to a blood vessel wall.

FIG. 30 shows an embodiment of bioabsorbable tip 23 positioned within first stage sealing material 67 in close proximity to blood vessel wall BVW. In this embodiment, bioabsorbable tip 23 may or may not extend through blood vessel wall BVW. Bioabsorbable tip 23 may extend at least partially through a hollow tract formed in first stage sealing material 67. As shown in FIG. 30, bioabsorbable tip 23 may extend along a distal portion of the hollow tract in first stage sealing material 67 and second stage sealing material 68 may be delivered to a proximal portion of the hollow tract in first stage sealing material 67 so that a proximal end of bioabsorbable tip 23 may contact second stage sealing material 68.

Figure 31:
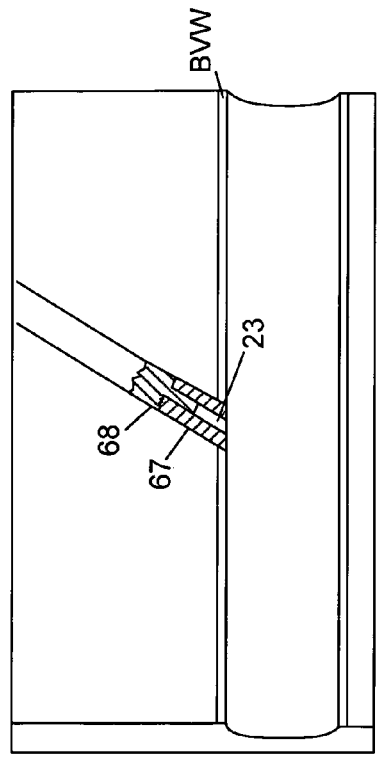
FIG. 31 illustrates an exemplary embodiment of a tip in contact with first stage sealing material and second stage sealing material.

FIG. 31 shows an embodiment of bioabsorbable tip 23 in contact with first stage sealing material 67 and second stage sealing material 68. Bioabsorbable tip 23 may extend at least partially through a hollow tract formed in first stage sealing material 67. Bioabsorbable tip 23 may extend along a proximal portion of the hollow tract in first stage sealing material 67 and a proximal end of bioabsorbable tip 23 may contact second stage sealing material 68.

Bioabsorbable tip 23 may connect to temporary sealing component 11 using one of a variety of attachment and/or release mechanisms. FIGS. 32-34 show exemplary embodiments of mechanisms provided to releasably attach bioabsorbable tip 23 to temporary sealing component 11.

FIG. 32 shows an embodiment of a mechanism for releasably attaching bioabsorbable tip 23 to temporary sealing component 11. Temporary sealing component 11 may include or may be attached to a structure 107. For example, structure 107 may be a distal end of wire 27 (FIG. 2) or may be attached to the distal end of wire 27. As shown in FIG. 32, a distal end of structure 107 may include an end member 108 having an outer dimension (e.g., width, thickness, diameter, etc.) that is larger than the corresponding dimension of structure 107. Bioabsorbable tip 23 may be molded around end member 108 so that bioabsorbable tip 23 includes an inner structure configured to receive end member 108 when bioabsorbable tip 23 is attached to structure 107. The geometry of end member 108 and/or the geometry of the molded inner structure of bioabsorbable tip 23 for receiving end member 108 may be modified to allow bioabsorbable tip 23 to detach from structure 107 with a desired release force, e.g., tensile force.

FIG. 33 shows another embodiment of a mechanism for releasably attaching bioabsorbable tip 23 to temporary sealing component 11. Temporary sealing component 11 may include or may be attached to a structure 109. For example, structure 109 may be a distal end of wire 27 (FIG. 2) or attached to the distal end of wire 27. As shown in FIG. 33, a distal end of structure 109 may include an end member 110 having an outer dimension (e.g., width, thickness, diameter, etc.) that is larger than the corresponding dimension of structure 109. Bioabsorbable tip 23 may be molded around end member 110 so that bioabsorbable tip 23 includes an inner structure configured to receive end member 110 when bioabsorbable tip 23 is attached to structure 109. The geometry of end member 110 and/or the geometry of the molded inner structure of bioabsorbable tip 23 for receiving end member 110 may be modified to allow bioabsorbable tip 23 to detach from structure 109 with a desired release force, e.g., tensile force.

FIGS. 34 and 35 show a further embodiment of a mechanism for releasably attaching bioabsorbable tip 23 to temporary sealing component 11. Temporary sealing component 11 may include or may be attached to a structure 111. For example, structure 111 may be a distal end of wire 27 (FIG. 2) or attached to the distal end of wire 27. As shown in FIGS. 34 and 35, structure 111 may include a surface that is configured to mate or engage with a corresponding surface on an end member 113 of bioabsorbable tip 23.

FIG. 34 shows the corresponding surfaces of structure 111 and end member 113 engaged so that bioabsorbable tip 23 is attached to temporary sealing component 11. When the corresponding surfaces are engaged, a tube 114 disposed around wire 27 may slide distally over the engaged surfaces of structure 111 and end member 113. As a result, tube 114 may cover and therefore lock the engaged surfaces of structure 111 and end member 113 together.

FIG. 35 shows bioabsorbable tip 23 detached from temporary sealing component 11. To detach bioabsorbable tip 23 from temporary sealing component 11, tube 114 is pulled back (in the proximal direction) away from the engaged surfaces of structure 111 and end member 113. Uncovered, the engaged surfaces of structure 111 and end member 113 may be separated (e.g., by pulling temporary sealing component 11 in the proximal direction or otherwise applying a tensile force), thereby releasing bioabsorbable tip 23 from temporary sealing component 11.

Another mechanism for releasably attaching bioabsorbable tip 23 to temporary sealing component 11 may include a member (not shown) formed of a material capable of breaking when sufficient tensile force is applied. For example, a member made of a polymer may attach bioabsorbable tip 23 to temporary sealing component 11, and the polymer may stretch when tensile force is applied. Necking may occur in the polymer when tensile force reaches a limit, which creates a break in the stretched polymer, thereby detaching bioabsorbable tip 23 from temporary sealing component 11. Tensile force may be applied when temporary sealing component 11 is pulled in the proximal direction and bioabsorbable tip 23 is held in place in first stage sealing material 67 and/or second stage sealing material 68.

Other mechanisms for releasably attaching bioabsorbable tip 23 to temporary sealing component 11 may include a cutting mechanism to cut off bioabsorbable tip 23, a pinching mechanism to release bioabsorbable tip 23, a pull wire to release bioabsorbable tip 23, a threaded member to release bioabsorbable tip 23, a mechanism that applies heat to cause separation of bioabsorbable tip 23 from temporary sealing component 11, etc. These mechanisms may be controlled to be able to cut or otherwise detach bioabsorbable tip 23 from temporary sealing component 11.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for sealing a puncture in a patient, the device including:
   a complete delivery device to deliver components to a vascular closure area, the delivery device, prior to delivery of components, comprising:
   a sealing component including:
      an elongate control member configured to pass through a puncture in skin of a patient,
      an expandable member disposed near a distal end of the elongate control member, and
      a tip releasably attached to the elongate control member distal to the expandable member; and
   a sealing material delivery component including:
      a delivery tube through which the elongate control member of the sealing component is configured to extend, the delivery tube being configured to deliver sealing material through an opening in a distal end of the delivery tubes;
   wherein the tip is configured to be detached from the elongate control member and remain within the sealing material.

2. The device of claim 1, wherein the delivery tube includes a first cavity configured to deliver a first sealing material to a location near the puncture in the patient when the expandable member in an expanded configuration abuts a surface defining a distal opening of the puncture.

3. The device of claim 2, wherein the delivery tube includes a second cavity, and the sealing component is configured to pass through the second cavity.

4. The device of claim 3, wherein the sealing component is configured to be removed from the second cavity in the delivery tube so that a second sealing material may be delivered through the second cavity to a location near the first sealing material in the patient.

5. The device of claim 1, wherein the sealing component includes a connector that is controllable to adjust the position of the sealing component with respect to the delivery tube of the sealing material delivery component.

6. The device of claim 1, wherein the elongate control member includes a lumen configured to direct fluid to the expandable member; and the tip is releasably attached to a distal end of a wire disposed in the lumen of the elongate control member.

7. The device of claim 6, wherein the sealing component further includes a sealing component coupling that connects to the wire and a proximal end of the elongate control member.

8. The device of claim 7, further including a sealing material delivery component coupling connected to the delivery tube and adjustably connected to the sealing component coupling.

9. The device of claim 1, further including a guide sheath through which the delivery tube and the elongate control member are configured to extend.

10. The device of claim 9, further including a guide sheath coupling that connects a hub of the guide sheath to the sealing material delivery component, the guide sheath coupling being controllable to adjust the position of the guide sheath hub with respect to the sealing material delivery component.

11. The device of claim 9, wherein:
the delivery tube includes a first cavity configured to deliver a first sealing material to a location near the puncture in the patient when the expandable member in an expanded configuration abuts a surface defining a distal opening of the puncture; and
the guide sheath is configured to deliver a second sealing material to a location near the first sealing material in the patient when the sealing component and the sealing material delivery component are withdrawn from the guide sheath.

12. The device of claim 1, further including a securement hub attachable to at least one of the delivery tube and a guide sheath through which the delivery tube and the elongate control member are configured to extend, the securement hub being placed against the skin of the patient.

13. The device of claim 12, wherein the securement hub includes a tube inserted into the patient and a luer fitting configured to direct fluid out of the patient.

14. The device of claim 1, wherein:
the expandable member of the sealing component is a first expandable member; and
the sealing material delivery component further includes a second expandable member attached to the delivery tube and configured to be expanded when located inside the puncture so that an outer surface of the second expandable member contacts at least one of an inner surface of a guide sheath surrounding the delivery tube or body tissue.

15. The device of claim 1, wherein the sealing component further includes an insert member disposed on the elongate control member proximal to the expandable member.

16. The device of claim 15, wherein the delivery tube is configured to deliver a first sealing material onto the insert member, the insert member forming a cavity in the first sealing material when the insert member is removed.

17. The device of claim 16, wherein the tip is configured to be positioned in the cavity and released from the sealing component.

18. The device of claim 16, wherein the insert member is configured to be in an expanded configuration when the first sealing material is delivered and in an nonexpanded configuration when removed from the cavity.

19. The device of claim 15, wherein the first sealing material is delivered to surround the distal end of the delivery tube to form a second cavity in the first sealing material when the delivery tube is removed; and the delivery tube or a guide sheath is configured to deliver a second sealing material to the second cavity.

20. The device of claim 1, wherein the tip is bioabsorbable.

21. The device of claim 1, wherein the tip includes a main body and at least one projection extending outward from the main body.

22. The device of claim 21, wherein the at least one projection includes one of a barb, a ring formed integrally with the main body, and a ring formed of a different material than the main body.

23. The device of claim 1, wherein the tip includes at least one of a suture, a disc, pliable material, an expandable material, and a stretchable braid.

24. The device of claim 1, wherein the tip includes at least one of a distal flange and a proximal flange.

25. The device of claim 1, wherein the tip is configured to be inserted into and extend at least partially through a cavity in a first sealing material delivered inside the patient through the delivery tube.

26. The device of claim 25, wherein the tip is configured to abut a surface of a second sealing material delivered inside the patient through the delivery tube or a guide sheath.

27. The device of claim 1, wherein the sealing component further includes a release mechanism configured to release the tip from the elongate control member.

28. The device of claim 27, wherein the release mechanism is configured to permit the tip from separating from the elongate control member due to a tensile force.

29. A sealing component for sealing a puncture in a patient, the sealing component including:
a complete delivery device to deliver components to a vascular closure area, the delivery device, prior to delivery of components, comprising:
an elongate control member configured to pass through a puncture in skin of a patient;
an expandable member mounted to a distal end of the elongate control member; a sealing material; and
a tip releasably attached to the elongate control member at a location distal to the expandable member and configured to be detached from the expandable member and remain within the sealing material at the puncture to at least partially seal the puncture.

30. The sealing component of claim 29, wherein:
the elongate control member includes a lumen configured to direct fluid to the expandable member; and
the tip is releasably attached to a distal end of a wire disposed in the lumen of the elongate control member.

31. The sealing component of claim 29, further including an insert member disposed on the elongate control member proximal to the expandable member.

32. The sealing component of claim 29, wherein the tip is bioabsorbable.

33. The sealing component of claim 29, wherein the tip is nonbioabsorbable.

34. The sealing component of claim 29, wherein:
the tip includes a main body and at least one projection extending outward from the main body; and
the at least one projection includes one of a barb, a ring formed integrally with the main body, and a ring formed of a different material than the main body.

35. The sealing component of claim 29, wherein the tip includes at least one of a suture, a disc, pliable material, an expandable material, and a stretchable braid.

* * * * *